United States Patent [19]

Beyer et al.

[11] 4,429,584

[45] Feb. 7, 1984

[54] MICROPROCESSOR CONTROLLABLE AUTOMATIC SAMPLER

[75] Inventors: William F. Beyer; Harry S. Dankert, both of Kalamazoo; James C. English, Schoolcraft, all of Mich.

[73] Assignee: The Upjohn Company, Kalamazoo, Mich.

[21] Appl. No.: 326,445

[22] Filed: Dec. 1, 1981

[51] Int. Cl.³ ............................................. G01N 35/06
[52] U.S. Cl. ............................. 73/864.21; 73/864.25; 422/64; 422/67
[58] Field of Search ........... 73/864.21, 864.22, 864.23, 73/864.25; 422/63, 64, 65, 67

[56] References Cited

U.S. PATENT DOCUMENTS

| | | | |
|---|---|---|---|
| 3,482,082 | 12/1969 | Isreeli . | |
| 3,546,946 | 12/1970 | Smith . | |
| 3,788,816 | 1/1974 | Rohrbaugh et al. | 422/64 |
| 3,842,679 | 10/1974 | Iwao et al. . | |
| 3,954,012 | 5/1976 | Christen et al. . | |
| 3,960,003 | 6/1976 | Beyer et al. . | |
| 4,038,874 | 8/1977 | Baldin et al. | 73/864.21 |
| 4,237,733 | 12/1980 | Kolb et al. | 73/864.21 |
| 4,253,846 | 3/1981 | Smythe et al. . | |
| 4,259,291 | 3/1981 | Smythe . | |
| 4,294,126 | 10/1981 | Tomoff | 73/864.25 |

Primary Examiner—S. Clement Swisher
Attorney, Agent, or Firm—Flynn, Thiel, Boutell & Tanis

[57] ABSTRACT

An apparatus for automatically establishing fluid communication between a probe and a plurality of containers presented in the sequence to a sampling position includes a container supported rack movable into and out of the sampling position. A probe holder supports the probe for movement into and out of the sampling position. A drive unit connects to the rack and probe holder for effecting and controlling the movements thereof. The drive unit includes a first pressure fluid operated motor actuable for moving the probe into and out of the sampling position for communication with a container thereat and a second pressure fluid operated motor actuable for causing the rack to move a desired one of the containers into the sampling position, the first and second pressure fluid operated motors being actuable independently of each other from a common source of pressure fluid. The apparatus is connectible to provide sequential samples for an analysis system, such as a high pressure liquid chromatography system. In a preferred embodiment the sampler apparatus includes an onboard microprocessor circuit programmable to control sequencing of the pressure fluid motors and timing of the chromatography system. This is in addition to an external computer for processing information resulting from analysis of the samples provided by the sampler apparatus.

15 Claims, 20 Drawing Figures

MICROPROCESSOR CONTROLLABLE AUTOMATIC SAMPLER

FIELD OF THE INVENTION

This invention relates to a system for establishing communication between a probe and sequentially presented sample containers, and more particularly to a sampler apparatus for controlling introduction of liquid samples to an analyzer system.

BACKGROUND OF THE INVENTION

The term "motor" is used herein generally, in the sense of a device to impart motion or apply force in response to an energy input thereto. In one embodiment disclosed below, motors of pressure fluid actuated rotary or linearly moving type are employed.

Automatic samples are known and have been employed in connection with automated high pressure liquid chromatography. However, we have found that it is possible to effect certain improvements in apparatus of this general type.

Accordingly, the objects of this invention include provision of:

An apparatus for sampling by a probe of sequentially presented containers on a movable rack in which movement of the rack as well as a probe is effected by pressure fluid operated motors in a housing supporting the probe and rack, in which actuation of the pressure fluid motors and other devices controlled to operate in sequence therewith, as for operating a liquid chromatography system, avoid the use of electromechanical relays, motors, limit switches, or other open electromechanical devices within the housing, and wherein generation of sparks and corresponding danger in use of readily ignitable volatile liquids as rinse or sample liquids is reduced.

Apparatus, as aforesaid, in which rack rotation and at least vertical probe movement are independently controllable through independent pressure fluid operated motors for maximum flexibility of moving one with respect to the other either manually for set-up purposes or to permit sampling of containers out of their sequence of arrangement on the rack.

Apparatus, as aforesaid, in which panel means within the housing are provided for onboard, internal location of a microprocessor circuit programmable to control sequencing of the pressure fluid motors moving the probe and sample rack, as well as a sample injection valve for a chromatography column, which onboard microprocessor circuit is in addition to and distinct from an external (host) computer of the type normally used for processing data from sample analyzing means such as a chromatographic detector.

Other objects and purposes and purposes will be apparent to persons familiar with apparatus of this general type upon reading the accompanying specification and inspecting the accompanying drawings.

The objects and purposes of this invention are met by providing apparatus for establishing fluid communication between a probe unit and a plurality of containers presented in a controlled sequence to a sampling position in which a rack unit is adapted to hold the containers for movement into and out of the sampling position and a hollow probe unit is supported by a probe holding unit and is movable thereby into and out of the sampling position. A drive connects to the rack unit and probe unit for effecting and controlling their movements. The drive includes a first pressure fluid operated motor actuable for moving the probe unit into and out of the sampling position for communication with containers thereat and a second pressure fluid operated motor actuable for causing the rack unit to move a desired one of the containers to the sampling position, the first and second pressure fluid operated motors being actuable independently of each other from a common pressure fluid source.

DETAILED DESCRIPTION

Figure 1:
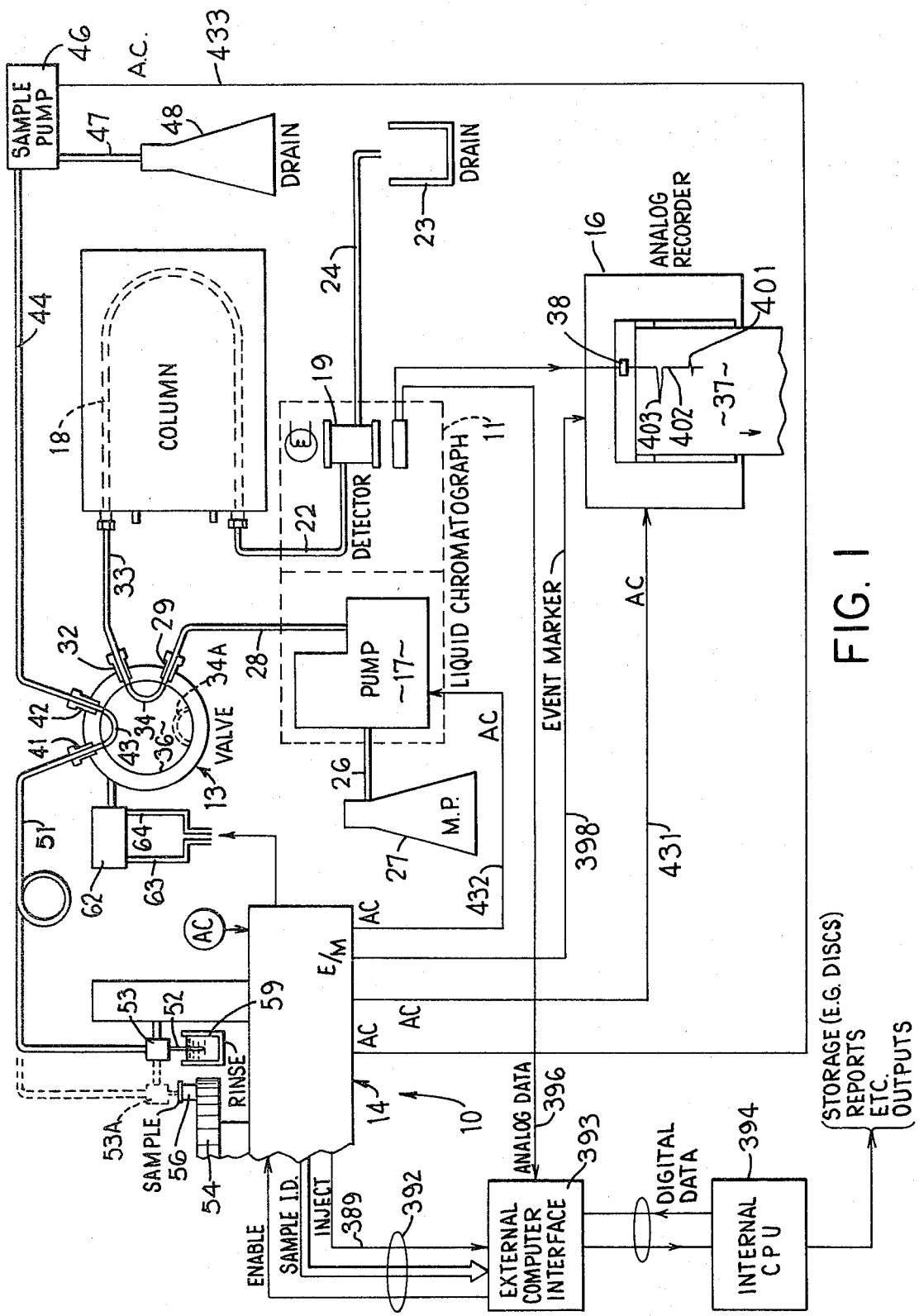
FIG. 1 diagrammatically discloses an automatic sampler 14 embodying the invention and controlling a high pressure liquid chromatograph system.

A preferred embodiment of the invention is disclosed, for purposes of illustration, in connection with a high pressure liquid chromatography (HPLC) system 10 (FIG. 1), though it will be understood that the sampler 14 and control system therein are readily usable in controlling non HPLC systems as well. Thus, the apparatus 10 (FIG. 1) here is comprised of a high pressure liquid chromatograph 11, a high pressure sampling valve 13, an automatic sampler 14 and a recorder 16, which may be provided with an integrator.

The chromatograph 11 may be of any conventional type and here includes a pump 17, a packed column 18 and a detector 19, the inlet of which is connected to the outlet end of the column 18 by a line 22. The outlet of the detector 19 is connected to a drain 23 by line 24. The detector 19, which may be an ultraviolet spectrophotometer or of other desired type, produces a signal which is transmitted to the recorder.

The pump 17 may be a constant volumn pump of any conventional type.

The inlet of the pump 17 is connected by line 26 to a supply of carrier liquid or mobile phase 27. The outlet of the pump 17 is connected by line 28 to one inlet port 29 on the valve 13. An outlet port 32 on the valve 13 is connected by line 33 to the inlet end of the column 18. A passageway 34 in the valve core 36 normally connects the inlet port 29 with the outlet port 32. The recorder 16 may be of any convenient type.

Said recorder 16 is equipped with a supply of graph paper 37 engaged by an inked stylus 38 in a conventional manner.

The valve 13 may be a high pressure sample valve of the type manufactured by Glenco Scientific, Inc. of Houston, Tex., and identified by Catalog No. SVOV-4-1X, capable of handling up to 3000 psi and equipped with an air actuator. Said valve 13 has an inlet port 41 and an outlet port 42 which are connected by passageway 43 in the core 36. The outlet port 42 is here connected by line 44 to a source of vacuum, such as the sample pump 46, the positive pressure side of said pump being connected by line 47 to drain 48.

The inlet port 41 of valve 13 is connected by line 51 to the probe 52 mounted upon the probe carriage 53. The sampler 14 includes a circular rack 54 mounted for rotation around a vertical axis and capable of supporting a plurality of test sample containers 56 which can be moved, one at a time, by rotation of the rack 54 into and, later, out of a position directly below the probe carriage, as shown in broken lines at 53A.

A supply of rinse liquid is provided to a rinse liquid receptacle 59 supported below the solid line position of the probe carriage 53. The carriage 53 moves the probe 52 upwardly out of the rinse receptacle 59, outwardly and then downwardly into a sample container. At a specified time, the probe 52 is moved upwardly, inwardly and downwardly into the receptacle 59. During this cycle, a sample is moved through lines 51, 44 and into passageway 43. After the valve 13 has been operated, as discussed hereinafter, the lines 51, 44 and passageway 43 are purged with rinse liquid.

The valve core 36 is rotated by the air actuator 62 between the position thereof shown in FIG. 1 with the passageways 34 and 43 in solid lines, and a position wherein passageway 43 is located in the position of passageway 34 and passageway 34 has moved down into the broken line position 34A. This operation, which is of relatively short duration, permits the movement of a portion of the test sample into line 33.

The lines 63 and 64 are connected to the opposite ends of the actuator 62 and through a solenoid valve to a source of compressed air.

The system to the extent described above with respect to FIG. 1 may be similar to the system disclosed in U.S. Pat. No. 3,960,003 assigned to the assignee of the present invention, and except for the improvements set forth below in connection with the sampler 14, the control apparatus included therein and the association therewith of an external data handling computer schematically indicated at 39A.

Figure 2:
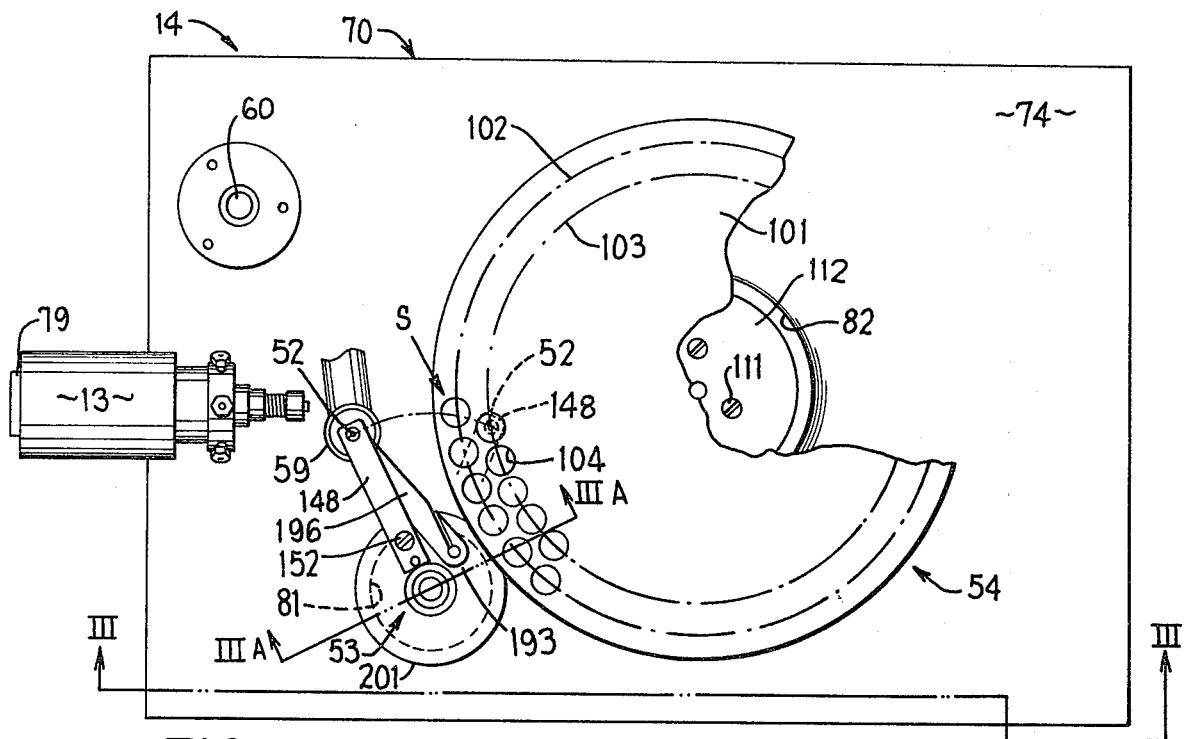
FIG. 2 is an enlarged top view of the sampler diagrammatically shown in FIG. 1 and with the probe in its rearward, rinse position.
Figure 8:
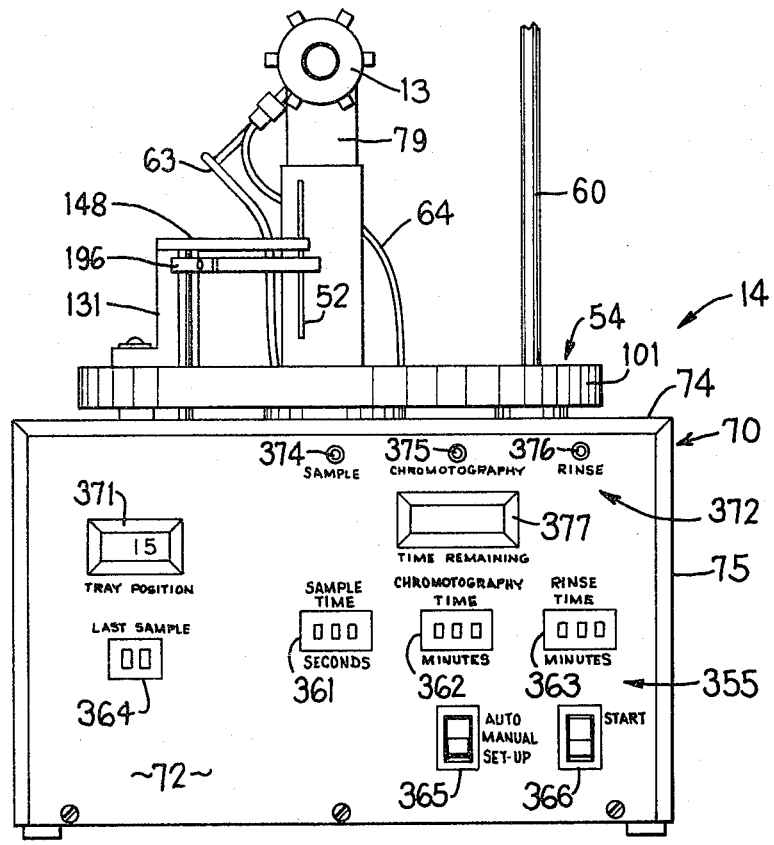
FIG. 8 is a front view of FIG. 2 sampler.

The sampler 14, in the preferred embodiment disclosed in FIG. 2 and thereafter, comprises a rectangular housing 70 including a floor 71 (FIG. 3) supporting upstanding front and rear exterior panels 72 and 73 (FIG. 5) and including a removable cover defined by a top wall 74 (FIG. 8) and side walls 75. Front and rear interior upstanding panels 77 and 78 (FIG. 5) are fixed to and spaced inboard of panels 72 and 73, respectively, for purposes appearing hereinafter.

A bracket 79 (FIGS. 2 and 3) fixedly upstanding from the rear panel 73 supports the sampling valve 13. A support rod 60 fixedly upstanding from the housing top 74 is provided for conventionally supporting a rinse liquid supply (not shown) leading to and terminating in the rinse liquid receptacle 59. Apertures 81 and 82 are provided in the top wall 74 (FIGS. 2 and 3) as hereafter discussed.

The rotatable rack 54 (FIGS. 2–4) here comprises an 80 place circular disklike sample tray 101 provided with concentric outer and inner rings 102 and 103 of recesses 104 for receiving sample containers of any convenient type accessible from the top thereof. In the particular embodiment shown, each ring 102 and 103 contains forty circumferentially evenly spaced recesses 104. To rotatably support the sample tray 101, a post 106 (FIG. 3) is fixed to and extends up from the floor 71 coaxially with the aperture 82, terminating below the top 74 and having an axial thrust collar 107 fixed thereto intermediate the floor 71 and top 74. A sleeve 108 has a top flange 109 fixed by screws 111 (FIG. 2) to an overlying sample holder plate 112. The sleeve 108 has a lower flange 114 to which is secured by screws in underlying, coaxial, forty tooth sprocket 116. The sleeve 108 is sleeved on the upper end of the post 106 for rotation coaxially thereof and is axially supported by the sprocket 116 on the collar 107, such that the sample holder plate 112 protrudes upward loosely through the aperture 82 in the top wall 74. The circular sample tray 101 sits in a lift off manner atop the plate 112 and coaxial and eccentric posts 121 and 122 atop the plate 112 are received in corresponding holes in the sample tray 101 for maintaining concentricity and permitting circumferential driving of the sample tray by means of the sprocket 116.

Figure 3:
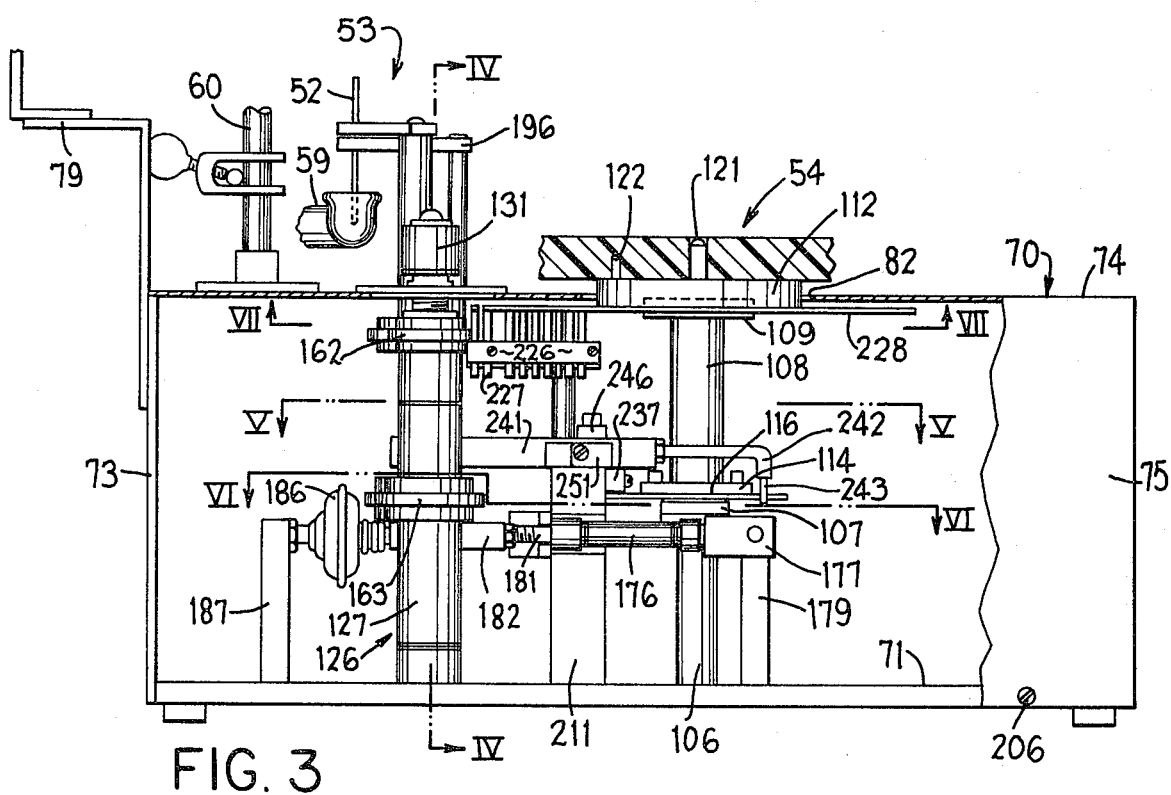
FIG. 3 is a partially broken, sectional view substantially taken on the line III—III of FIG. 2.
Figure 3A:
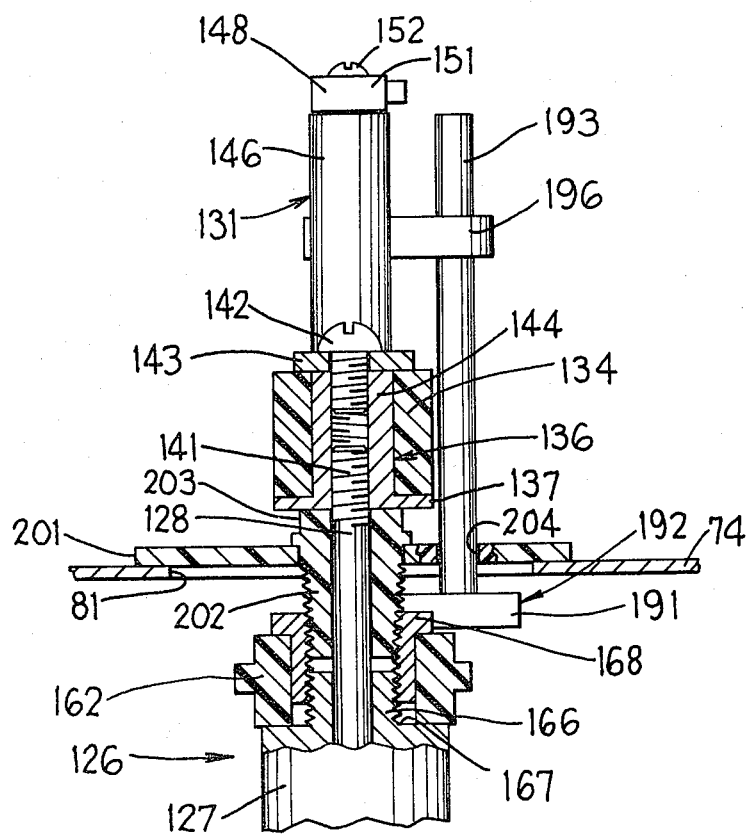
FIG. 3A is an enlarged partially broken fragment of the FIG. 2 probe carriage substantially as taken in the direction III—III of FIG. 2.
Figure 4:
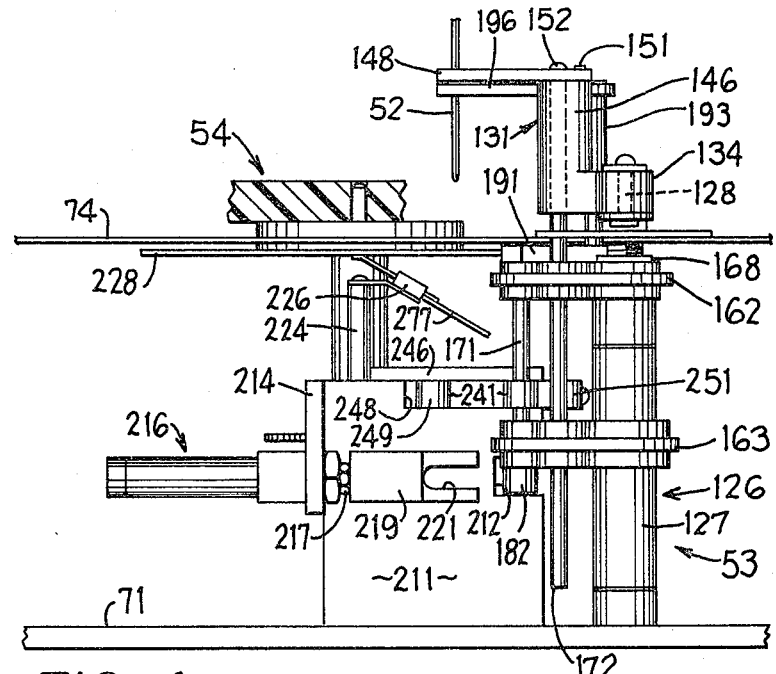
FIG. 4 is a partially broken sectional view substantially as taken on the line IV—IV of FIG. 3 but with the probe carriage in an intermediate horizontal position, and with the horizontal scale of the drawing stretched to better show the relationship of parts.

The probe carriage 53 comprises a vertical axis pressure fluid cylinder 126 (FIGS. 3, 4 and 5) having a casting 127 fixed to and upstanding from the floor 71 substantially coaxially beneath the aperture 81 in the housing top 74. The piston rod 128 (FIGS. 5 and 6) of the cylinder 126 extends reciprocably upward from the casing 127 of the pressure fluid cylinder 126 and loosely through the aperture 81 in the housing top wall 74. Vertically adjustably mounted atop the threaded upper end of the piston rod 128 is the horizontal leg of a substantially L-shaped sample head 131 (FIGS. 3, 3A and 4). More particularly, the horizontal leg 134 of L-shaped member 131 is vertically bored to rotatably receive a "nut" 136. The nut 136 here comprises an internally threaded sleeve having a radially extending bottom flange 137 and vertically threadably adjustable on the threaded upper end 141 of the piston rod 128. The nut 136 further includes a screw 142 and associated washer 143 threaded in the sleeve for clamping the horizontal leg 134 of the L-shaped member axially. By providing flats (not shown) on the periphery of the flange 137, the screw 142 can be tightened snugly against the end of the central sleeve portion 144 of the nut 136 while still permitting the nut to rotate within the horizontal leg 134, so as to threadedly adjust up and down the leg 134 on threaded upper end 141 of the piston rod 128 and thereby vertically adjust the position of the L-shaped member 131 with respect to the piston rod.

A sample arm 148 is fixed at one end atop the vertical leg 146 by a locator pin 151 and screw 152 and extends in cantilevered relation therefrom to releasably grip and support, through a set screw connection not shown, the hollow probe 52 (FIG. 4). Thus, vertical reciprocation of the piston rod of the vertical pressure fluid cylinder 126 correspondingly raises and lowers the sample head 131 and hollow probe 52 carried thereby.

The probe carriage 53 is also capable of pivoting the probe 52 in a horizontal plane. More particularly, upper and lower bushing arms 162 and 163 are each pivoted on one end thereof on the casing 127 of the upstanding pressure fluid cylinder 126, for horizontally pivoting about the vertical axis of the cylinder (FIGS. 3, 3A and 4). The lower bushing arm 163 pivots directly on the periphery of the pressure fluid cylinder casing 127 and is vertically positioned by means hereafter discussed. The upper end 166 of the cylinder casing 127 is reduced in diameter to form a step and is externally threaded. A top flanged internally threaded sleeve is threaded on the cylinder end 166, pivotally receives the end of the bushing arm 162 thereon and vertically locates it against the upward facing step 167, to freely pivot thereon.

Upstanding outer and inner guide rods 171 and 172 (FIG. 4) are coplanar with and parallel to the vertical axis of the pressure fluid cylinder 126 and respectively extend upward through the outer ends, and intermediate portions, of the upper and lower bushing arms 162 and 163. The outer guide rod 171 is substantially a press fit in the outer ends of the bushing arms 162 and 163 and thus controls the vertical level of lower arm 163 and maintains the two arms 162 and 163 vertically aligned. The inner rod 172 extends snugly but slidably up through the middle portions of the arms 163 and 162 and thence upward in fixed relation through the height of the upstanding arm 146 of the L-shaped member 131. In the embodiment shown, the screw 152 securing the arm 148 on the L-shaped member threadedly engages the upper end of the rod 172 to interlock the rod 172, arm 148 and leg 146 of L-shaped member 131. In this way, the arm 148, the horizontal leg 128 of the L-shaped member 131 and the arms 162 and 163 all extend in the same horizontal direction from the axis of the pressure fluid cylinder 126, i.e. are centered on a common vertical plane therethrough.

To horizontally pivot the arms 148, 162 and 163, a horizontal pressure fluid cylinder 176 (FIGS. 3 and 5) has the rear end 177 of its casing mounted for pivoting about a vertical axis atop a post 179 fixedly upstanding on the floor 71. The pressure fluid cylinder 176 extends from the post 179 leftwardly toward the outer guide rod 171, the piston rod 181 of the cylinder 176 having threadedly fixed thereon, preferably for axial adjustment, an extension member 182 which at its free (leftward in FIGS. 3 and 5) end is pivotally engaged with the lower end of outer rod 171, such that extension and retraction of the piston rod 181 of the pressure fluid cylinder 176 pivots the inner connected arms 148, 162 and 163 about the axis of the vertical pressure fluid cylinder 126, to swing the arm 148 and therewith to swing the probe 52 between its solid line rinse position and dotted line sample position of FIG. 2. A dashpot 186 is fixed atop a post 187 in turn fixed atop the floor 71 to damp the end portion of the extension movement of the piston rod 181 so as to avoid shock to the probe 52 in swinging into position over the rinse receptable 59.

The upper end of the outer rod 171 (FIG. 4) terminates in and is fixed to the free end of the horizontal leg 191 of a substantially L-shaped member 192 having a rodlike upstanding leg 193 at the remote end thereof, as seen in FIGS. 3A and 4. Clamped adjustably (both vertically and circumferentially) to the upstanding rodlike leg 193 is one end of a sample stripper arm 196 (FIGS. 2 and 3) the free end of which is perforated for loose passage of the probe 152 downward therethrough. The arm 196 moves horizontally (pivotally) with the sample arm 148 but is vertically fixed and may be set at many desired height on on the rodlike leg 193 so as to closely overlie the tops of vials or containers on the sample tray 101. Thus, where vials or containers having closed upper ends, which are pierced by the probe 52, may tend to rise with the probe as it rises after sampling, the stripper arm 196 serves to strip the vial of the rising probe 52 so that such vial will maintain its position on the sample tray 101.

A circular cover plate 201 (FIGS. 2 and 3A) removably covers the aperture 81 in the housing top wall 74 for preventing falling of foreign materials into the interior of the housing. The cover plate 201 is held snug against the upper side of the housing top wall 74 by a radially flanged keeper sleeve 202 which sleeves over the piston rod 128 and is externally threaded to grip the interior of sleeve 168. Flats 203 on the upper end of the sleeve 202 permit unthreading thereof from the sleeve 168. Holes (one of which is shown at 204 in FIG. 3A) through the plate 201 snugly but slidably receive the rods 172 and 193 (FIG. 4) upward therethrough.

The probe supporting structure shown in FIGS. 3A and 4 simplifies the removal of the cover 74, 75 from housing when access is desired to components within the housing. To remove the cover 74, 75, stripper arm 196 is removed (as by loosening a set screw not shown) upward from the rod 193 (FIG. 3A). The screw 152 is removed and the nut 136 (comprising elements 137 142, 143, 144) is rotated within the L-shaped member 131 and thereby threaded up off the upper end of the piston rod 128, thereby permitting lifting of the L-shaped member 131 off the top of the rod 172 (FIG. 4). The keeper sleeve 202 is then threaded up out of the sleeve 168 and off the top of piston rod 128, which permits upward lifting of the cover 201 off the housing top wall 74 and beyond the upper ends of the piston rod 128 end rods 172 and 193. Thereafter the sample tray 101 (FIG. 2) can be simply lifted off the top of its holder plate 112. Upon removal of holding means such as screws 206 (FIG. 3) securing the housing cover 74, 75 to the housing floor 71, the housing cover can then simply be lifted off the bottom portion of the housing.

Figure 5:
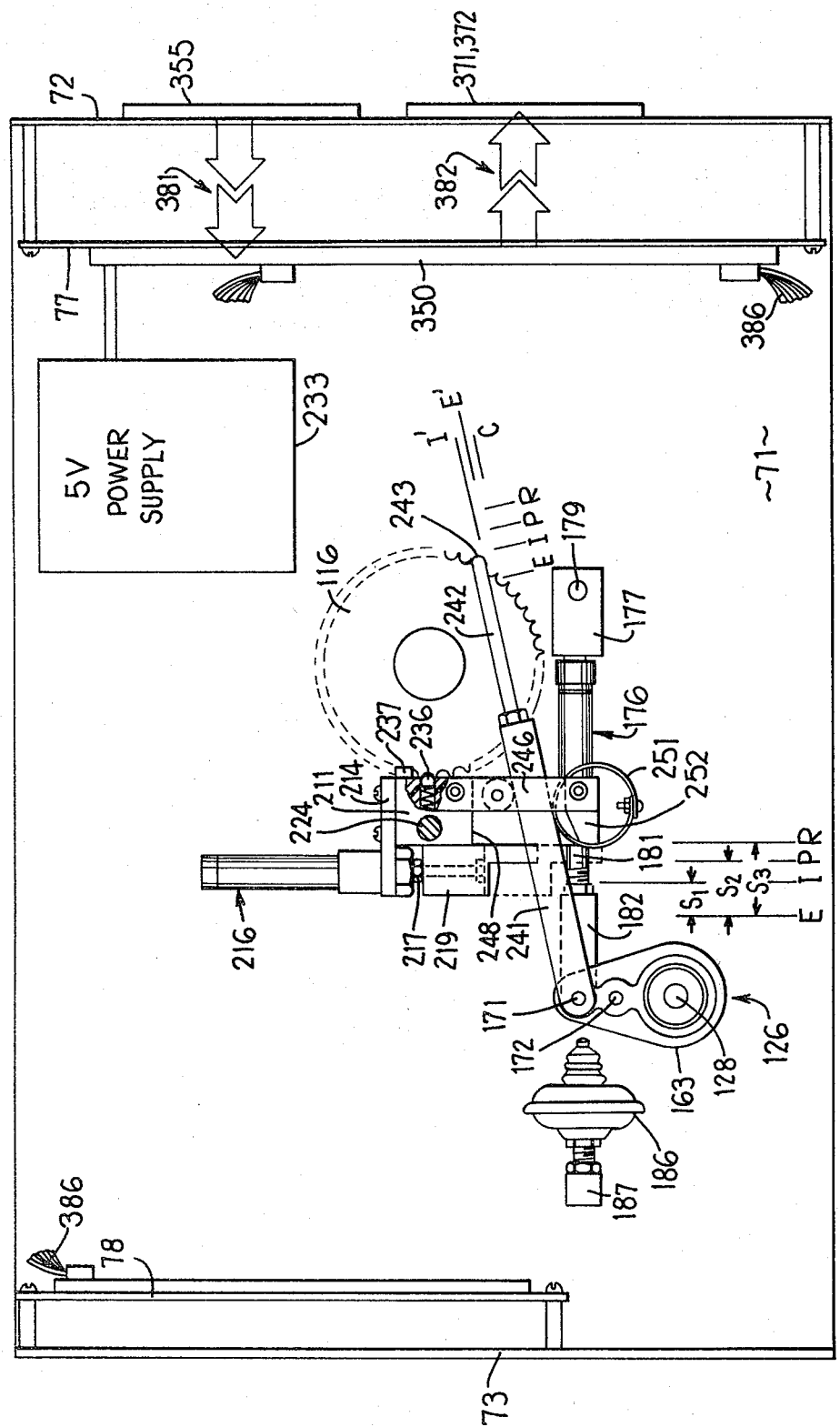
FIG. 5 is a sectional view substantially taken on the line V—V of FIG. 3.

Fixedly upstanding from the center portion of the floor 71, within the housing, is a mounting block 211 (FIGS. 3–6). In the embodiment shown, the block 211 is substantially rectilinear, though the block may be shaped as desired. The pressure fluid cylinder 176, which supports extension member 182, extends past one end (rightward in FIG. 4) of the block 211 and in the embodiment shown the block 211 is relieved thereat as indicated at 212. A mounting plate 214 (FIGS. 4 and 5) extends rearward from the opposite end of the block 211 and supports a further horizontal pressure fluid cylinder 216, the piston rod 217 of which has fixed thereon a forked wedge member 219 slidably guided along the rear side of block 211, from its solid line position of FIG. 5 to its dotted line position therein, for receiving the piston rod 181 of cylinder 176 in the notch 221 of its forked leading end. As seen in FIG. 5, the forked wedge 219 in its solid line retracted position permits a full length (of length $S_3$) retraction stroke of the piston rod 181 to move the probe 52 from above rinse liquid container 59 (FIG. 2) to above a container in the inner circumferential row 103. The forked wedge 219 in its dotted line extended position of FIG. 5 prevents full retraction of the piston rod 181 (limiting the retraction stroke as indicated at $S_2$ in FIG. 5), so that the probe 52 can swing horizontally from the rinse liquid receptacle 59 (FIG. 2) only over to the outer row of containers 102. Thus, the cylinder 216 controls which of the two rows of containers 102 and 103 will be sampled by the probe 52.

Figure 7:
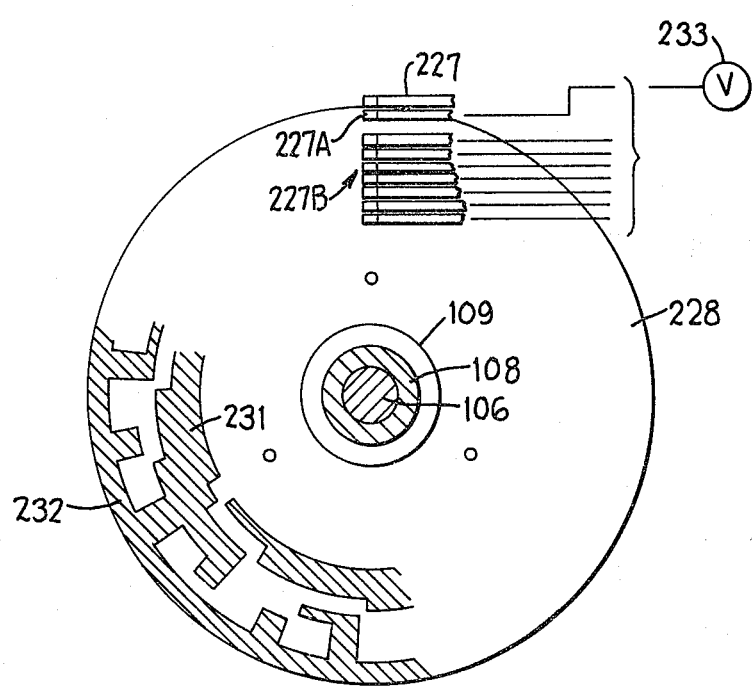
FIG. 7 is a sectional view substantially taken on the line VII—VII of FIG. 3

A post 224 fixed to and upstanding from the block 211 carries a contact finger bracket 226 in turn insulatingly supporting a plurality of electrically conductive fingers 227 (FIGS. 3, 4 and 7). An insulative disk 228 is fixed to the underside of the sample holder plate 112 and on its underside carries an electrically conductive pattern 231 (FIG. 7) in a preselected circumferentially matched relation with the individual container locations 104 on the sample tray. The conductive (preferably printed circuit) pattern 231 includes a circumferentially continuous outer edge portion 232 supplied with a ground potential from a strobed circuit voltage source generally indicated at 233 from one of the radially outer fingers, indicated at 227A. Radially inwardly disposed ones 227B of the fingers, in combinations dependent on the circumferential position of the disk 228, variously engage overlying portions of the conductor pattern 231. Such the fingers 227B, taken as a group, carry a unique binary coded voltage pattern for each of the forty possible circumferential positions of the sample tray 101 with respect to the probe 52, such that the binary coded voltage output of the fingers 227B identifies the particular container position which is then registrable with the probe 52. The fingers 227 and disk 228 are purchased units available from Hewlett Packard, located at Avondale, Pa. and Graphic Services of Jennison, Mich., respectively.

To resiliently lock the sprocket 116 against unintended circumferential movement, between times when a new container is being advanced into sampling position, the block 211 carries a spring-loaded detent ball 236 (FIG. 5) receivable between an opposed pair of teeth of the sprocket. The block 211 fixedly carries a retainer element 237 (FIGS. 3 and 5) which closely overlies the sprocket 116 adjacent the detent ball 236 to prevent the sprocket 116 and therewith the remainder of the rotating assembly from rising upward out of its operating position shown in FIG. 3.

A ratchet arm 241 (FIGS. 3-5) is provided for circumferentially advancing the sprocket 116 and therewith the sample tray 101 in response to extension of the pressure fluid cylinder 116. More particularly, the ratchet arm 241 is pivoted at one end on the upstanding rod 171. The intermediate portion of the ratchet arm 241 is guided across the top of the block 211 as hereafter discussed and terminates in an axially extending, axially adjustably mounted, generally L-shaped sprocket actuating portion 242, the depending tip 243 (FIG. 3) of which is engageable in the groove between adjacent teeth of the sprocket 116 to clockwise advance the sprocket 116 to the next tooth position upon each extension of the pressure fluid cylinder 116. As seen in FIGS. 4 and 5, the middle portion of the ratchet arm 241 is guided against vertical movement by an overlying transverse bar 246 affixed atop the block 211 to cover an upward opening notch 248 through which the ratchet arm slidably extends. The middle portion of the ratchet arm 241 is guided to permit limited sideways rocking movement by vertical axis rotatable roller 249 and a leaf-spring loop 251 disposed on either side thereof within the notch 248. The roller 249 is rotatably supported on the block 211. The spring loop 251 is supported for resilient flexing sidewardly of the ratchet arm 241 by being sleeved over an upstanding portion 252 of the block 211 at the corresponding end of the notch 248. The portion 252 of the block extends almost the diameter of the loop 251 in a direction substantially parallel to the length of the ratchet arm 241 but is of width considerably less than the diameter of the spring loop 251 in a direction horizontally transverse of the arm 241, as seen in FIG. 5. In this way, some sideward movement and rocking of the ratchet arm 241 is permitted due to pivoting of the upstanding rod 171 at one end thereof about the axis of the upstanding cylinder 126, and due to movement of the depending end 243 with the rim of the sprocket 116 during circumferential incrementing thereof by one tooth period of the sprocket 116. In FIG. 5, the pressure fluid cylinder 176 is shown in a position of partial extension, beyond the point of normal retraction or retraction limited by the forked wedge 219 in its dotted line position, but prior to completion of pivoting of the arm 163 fully counterclockwise (to the rinse position of FIG. 2), such that the piston rod 181 still has the last portion of its leftward extension travel to complete. It is during this portion S1 of the travel that the ratchet arm 241 clockwise advances the sprocket 116 by one tooth width. Such extension of piston rod 181 is completed by abuting of its extension 182 against the snubber 186 so as to gently decelerate, prior to stopping, the piston rod 181 and ratchet arm 241, so as to resist any tendency of the sprocket 116 to circumferentially overshoot the detent ball 236 and thus to prevent circumferential advancement of the sprocket involuntarily by more than one tooth width.

Summarizing, FIG. 5 illustrates by letter four positions of the piston rod 181 and the four corresponding positions of the ratchet arm 241 driven thereby, namely the fully retracted position R of the piston rod 181 corresponding to withdrawal of the forked wedge 219 to its solid line position of FIG. 5 and positioning of the probe 52 over the inner ring 103 of containers; the partially retracted position P of the piston rod 181 determined by the dotted line extended position of the forked wedge 219 and to the positioning of the probe 52 over the outer ring 102 of containers; the intermediate position I in which the piston rod 181 is actually shown in FIG. 5 and wherein the end 243 of the ratchet arm 241 is engaged a tooth of the sprocket 116 preparatory to circumferentially advancing the sprocket; and the fully extended position E of the piston rod 181 corresponding to completion of one tooth circumferential advancement of the sprocket 116 by the ratchet arm 241 and snubbing of the piston rod extension 182 by the snubber 186.

While the embodiment above-described conveniently employs the same pressure fluid cylinder 176 both for pivoting horizontally the probe 52 and circumferentially advancing the next container in either ring 102 or 103 into sampling position, it may at times be desired to sample in sequence containers out of their sequence of circumferential arrangement in ring 102 or 103. This is readily handled in the above-described apparatus by simply cycling the pressure fluid cylinder 116 through the desired number of extensions and retractions, so as to circumferentially advance the sprocket 116 the required number of sequential steps to bring the next desired container into sampling position, while leaving the piston rod of the vertical cylinder 126 in its raised position, permitting horizontal swinging of the probe 52 without interference with the rinse receptacle 59 or containers on the sample tray 101.

Figure 12:
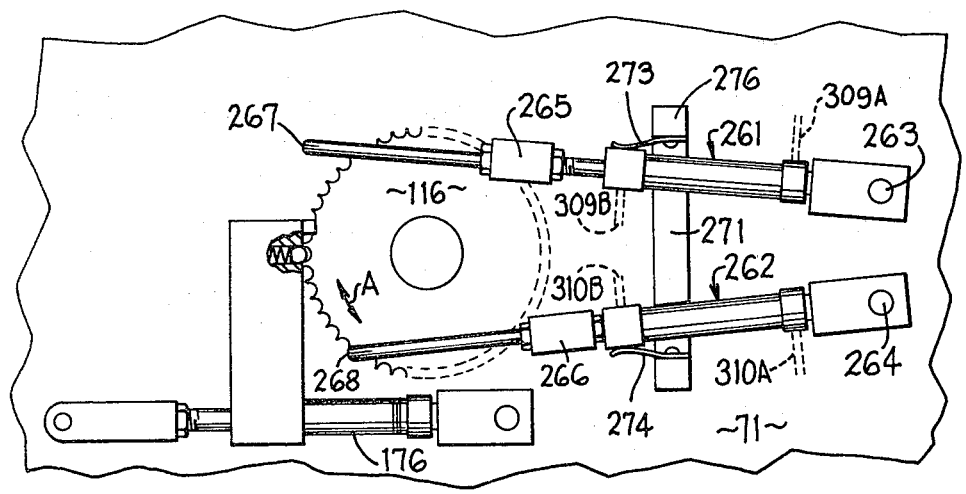
FIG. 12 is a top view, corresponding to a fragment of FIG. 5, but showing a modified rack drive.

However, it is contemplated that there may be instances in which it is desirable to make independent the movement of the sprocket wheel 116 and the movement of the probe 2. The modification of FIG. 12 provides for this possibility by eliminating the ratchet arm 241 and instead providing two additional pressure cylinders 261 and 262 mounted on vertical axis pivots 263 and 264 upstanding from the floor 71 and having piston rods extended by respective ratchet arms 265 and 266 respectively terminating (like above-described ratchet arm 241) in depending fingers 267 and 268 respectively engageable with teeth of the sprocket 116. The axes of the pressure fluid cylinders 261 and 262 extend substantially side by side on opposite sides of the sprocket center and with the ratchet arms 265 and 266 extending substantially chordally on opposite sides of the sprocket 116. A central abutment 271 separates the pressure fluid cylinders 261 and 262 and prevents same from moving too close to the center of the sprocket 116, while fixed leaf springs 273 and 274 resiliently limit swinging of the pressure fluid cylinders 261 and 262 sidewardly away from the center of the sprocket 116. If desired, the support 276, fixed upon the floor 71, assists in the vertical support of the bodies of the cylinders 261 and 262. Normally, the piston rods of both cylinders 261 and 262 will be extended (the position shown in FIG. 12 for cylinder 261). Then, retracting either cylinder 261 or 262 (cylinder 262 being shown with its piston rod retracted) rotates sprocket 116 either clockwise or counterclockwise one tooth width, as indicated by the arrow A. In this way, sequential retraction cycles of the cylinder 261 will increment the sprocket 116 clockwise by a corresponding number of teeth. Sequential retraction of the pressure fluid cylinder 262 a given number of times will, in contrast, increment the sprocket 116 counterclockwise a corresponding number of teeth. The sprocket 116 is thus not only incrementable, as desired either clockwise or counterclockwise, but is incrementable without actuation of the pressure fluid cylinder 176 and consequently without swinging of the probe 52 between rinse and sampling positions. On the other hand, the pressure fluid cylinder 176 is actuable to extend or retract without any corresponding movement of the sprocket 116, should it be desired to swing the probe 52 from rinse position to a container in outer row 102, back to rinse position and thence to a container in inner row 103, for example.

Figure 6:
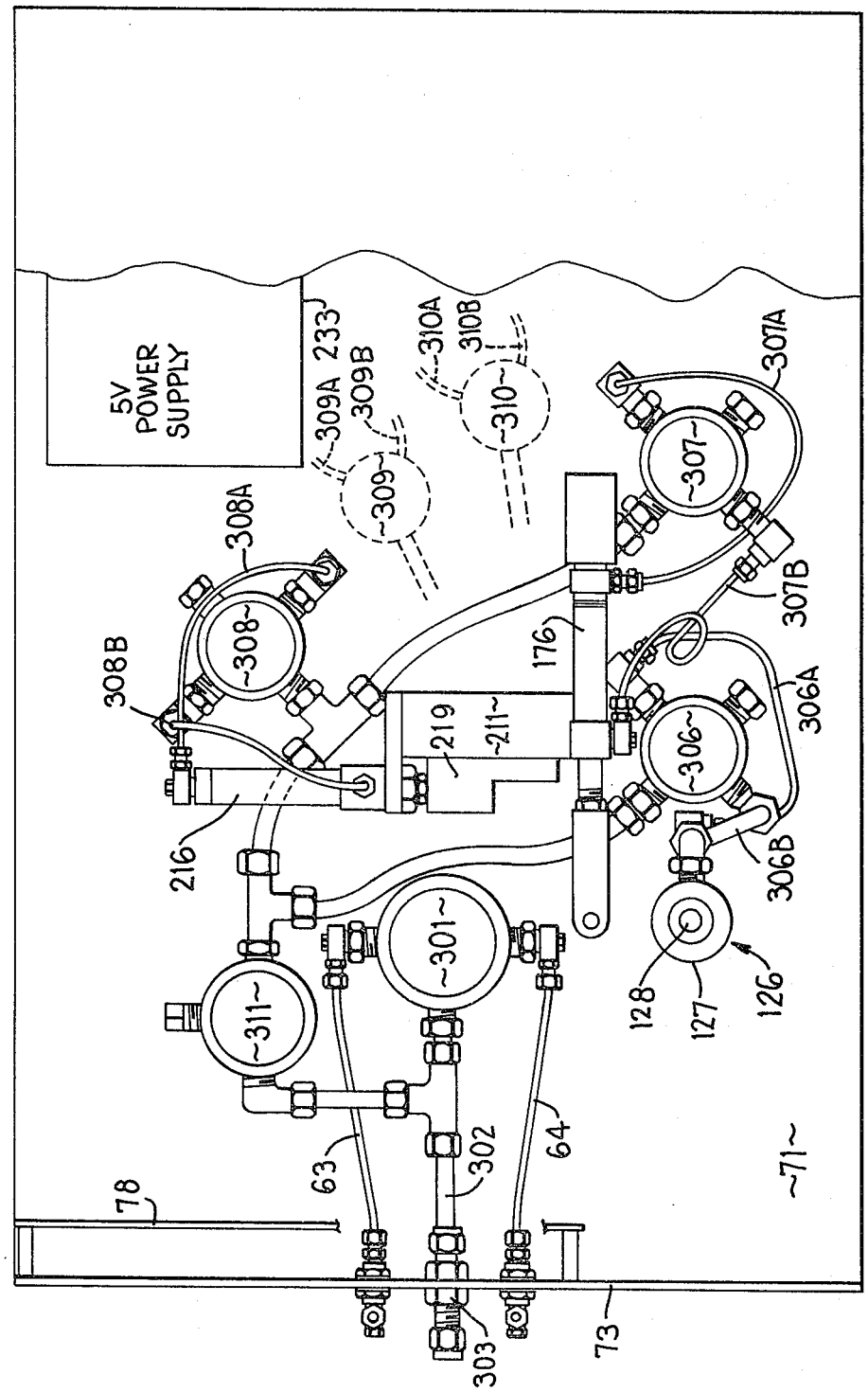
FIG. 6 is a sectional view substantially taken on the line VI—VI of FIG. 3.

Mounted on the floor 71 within the housing, as seen in FIG. 6, are a four-way single solenoid valve 301 fed through an air line 302 from a pressurized air supply (not shown) connected thereto by a fitting 303 through the back wall 73 of the housing. Three additional four-way double solenoid valves 306, 307 and 308 are supplied pressurized air from the conduit 302 through an air pressure regulator 311. The solenoid valves 301 and 306-308 are conventional units available from Humphrey Products of Kalamazoo, Mich. The regulator 311 is a conventional unit available from Master Pneumatic of Detroit, Mich.

Solenoid valve 301 is electrically actuable to alternately apply air pressure through the lines 63 and 64 to place the injection valve 13 (FIG. 1) in either of its two alternative positions above-described.

Similarly, solenoid valves 306, 307 and 308 are respectively electrically actuable to alternately apply air pressure to either of their respective output lines 306A or 306B, 307A or 307B and 308A or 308B to extend or retract their corresponding pressure fluid cylinders 126, 176 and 216.

Additional solenoid valves, similar to valves 306-308 are, as schmetically indicated in dotted line at 309 and 310, connected for electrical actuation to alternatively extend and retract the pressure fluid cylinders 261 and 262, respectively, by controlling air pressure in lines 309A, 309B, 310A and 310B leading to such cylinders, if the FIG. 12 modification is adopted.

It is contemplated that the apparatus to the extent above described can be operated manually, to carry out high pressure liquid chromatography, as by manual control of electrical inputs to the FIG. 6 solenoids, and by manual actuation of the mobile phase pump 17 (FIG. 1), sample (vacuum) pump 46, and the recorder 16, for example. Also, it is contemplated that the above-described apparatus can be controlled by a hard wired control circuit, for example utilizing conventional timers, relays, and the like, of the general type disclosed in U.S. Pat. No. 3,960,003, assigned to the assignee of the present invention. Alternatively, fluidic circuitry can be employed to control fluid actuators at 13, 17, 46, 126, 216, 176, 261 and 262.

Figure 14:
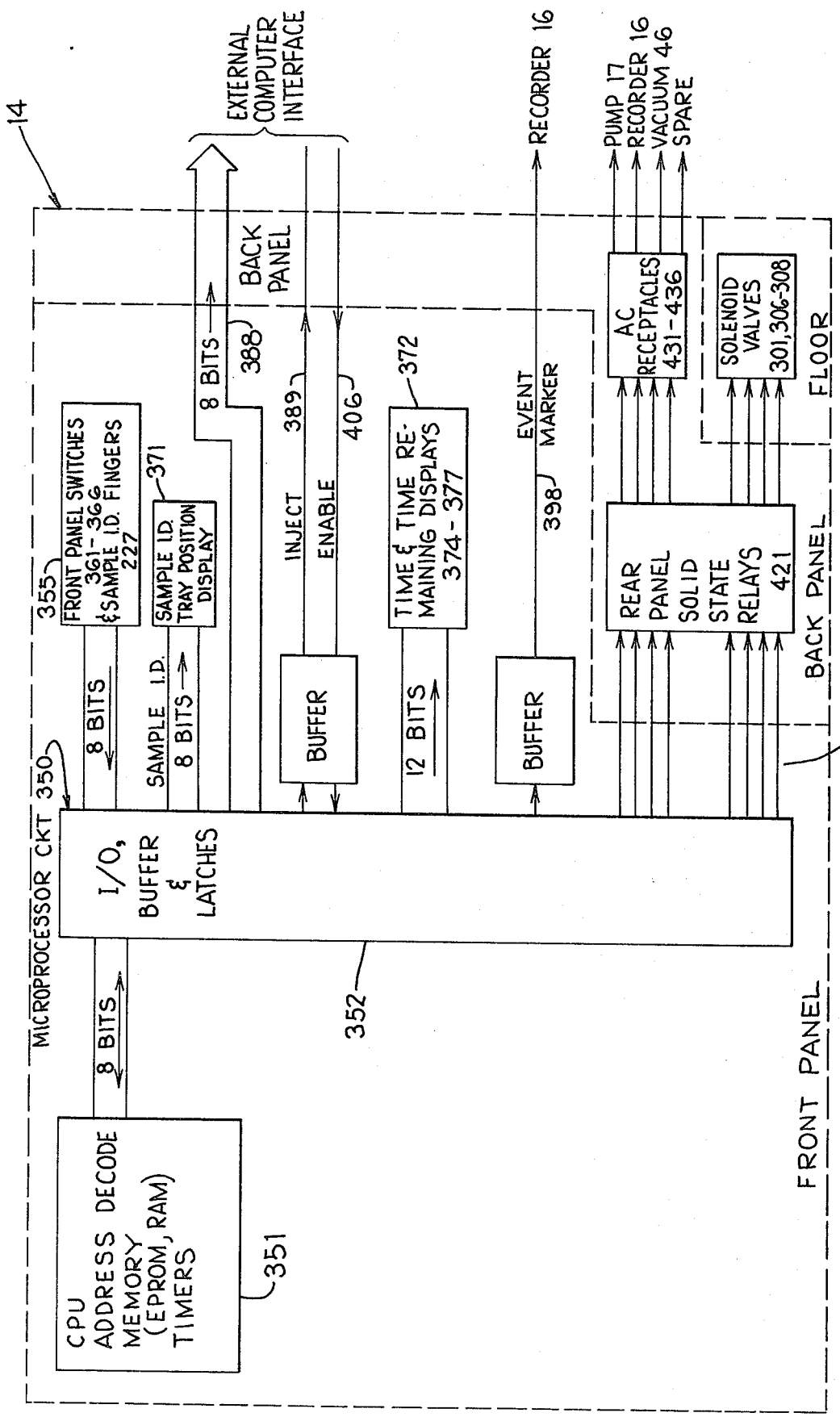
FIG. 14 is a block diagram of the microprocessor circuit with its inputs and outputs.
Figure 15A:
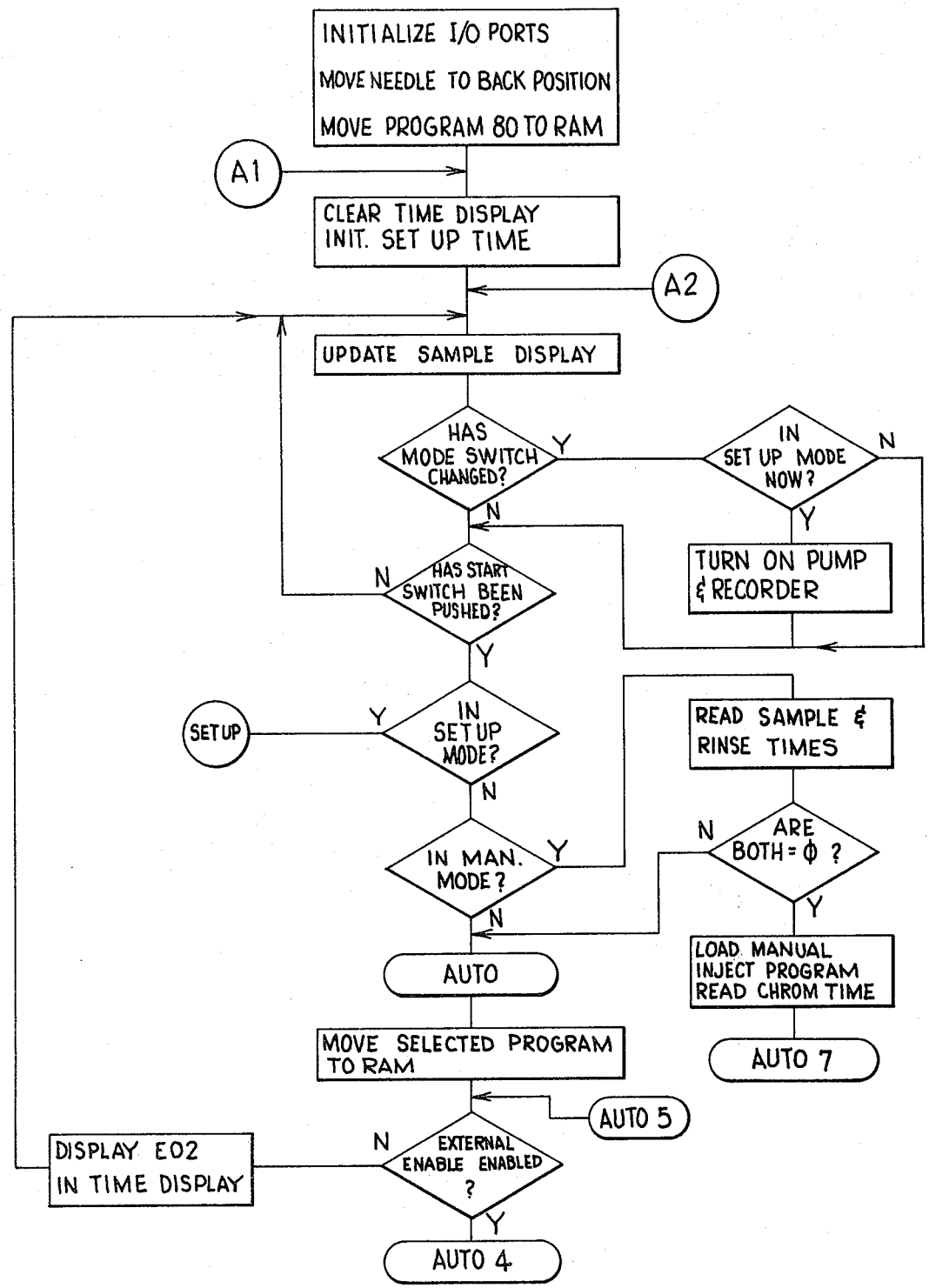
FIG. 15 A-E is a flow chart indicating one way of programming the microprocessor circuit of FIG. 14.
Figure 15B:
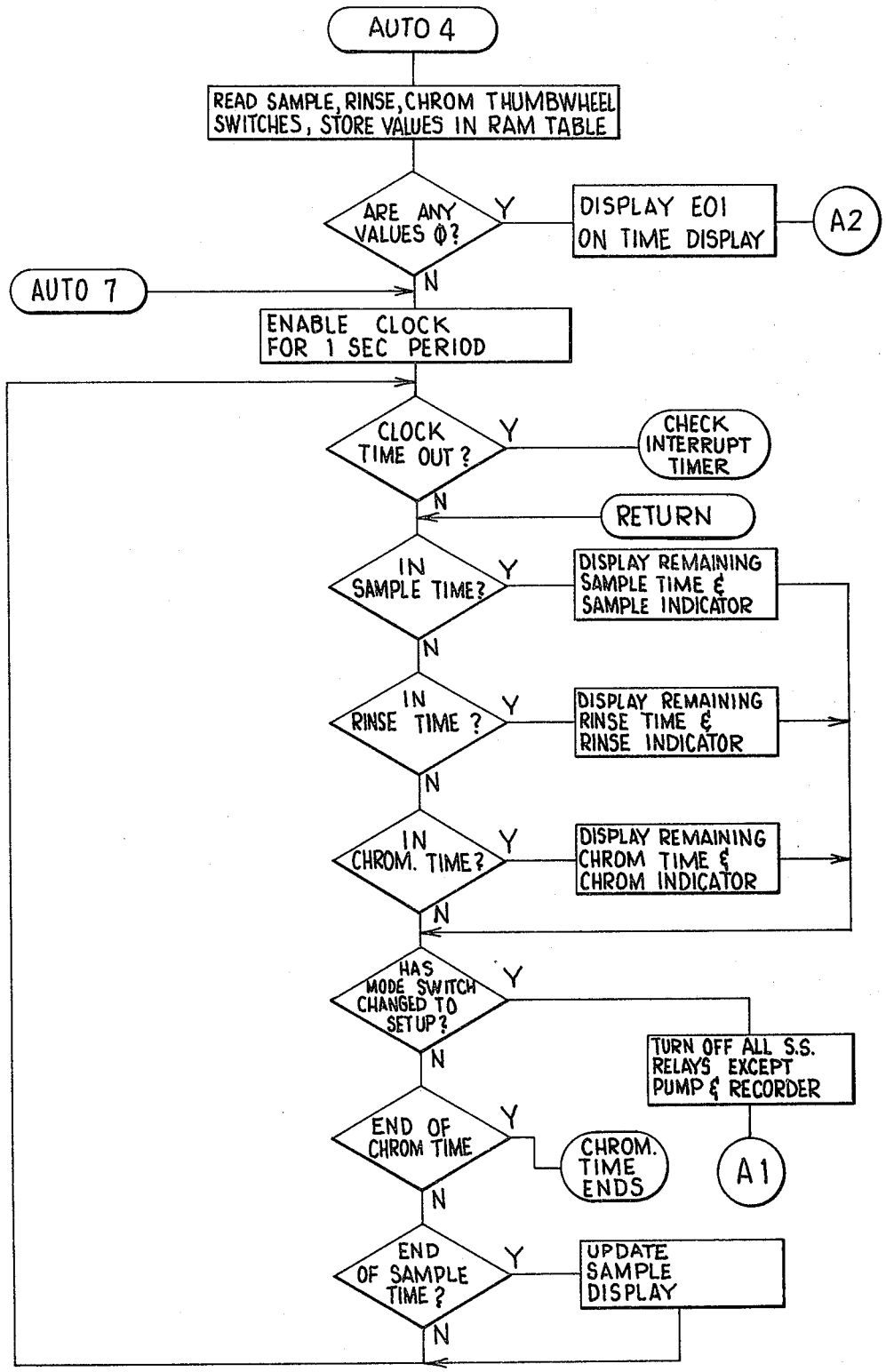
Figure 15C:
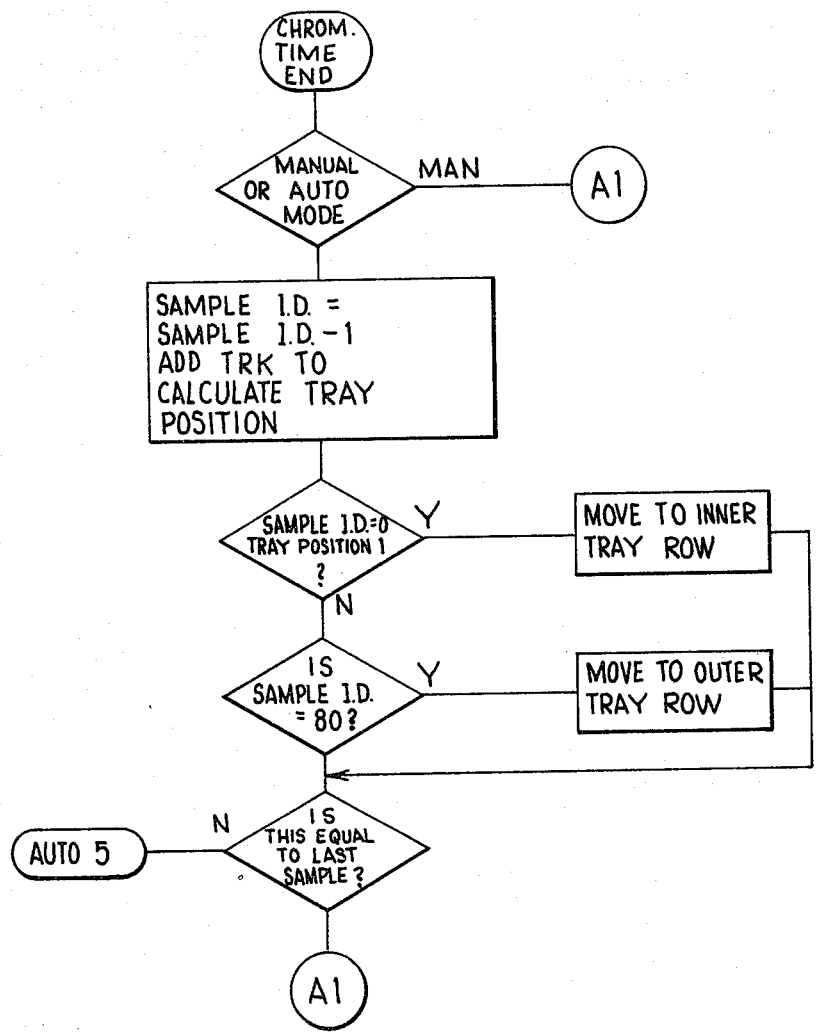
Figure 15D:
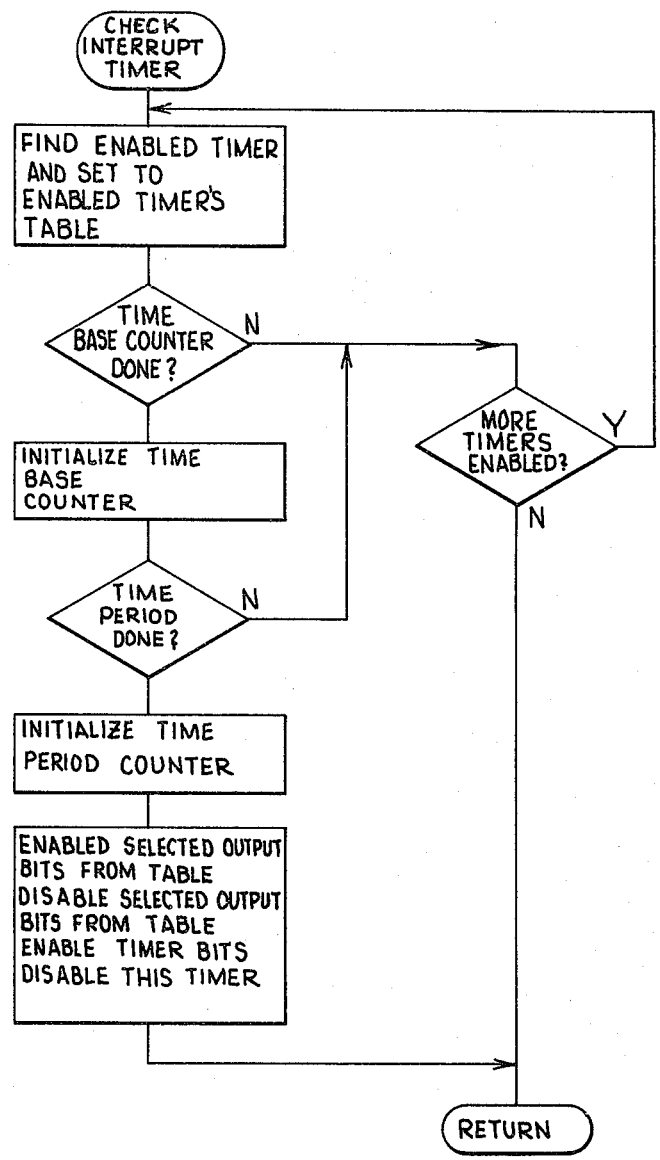
Figure 15E:
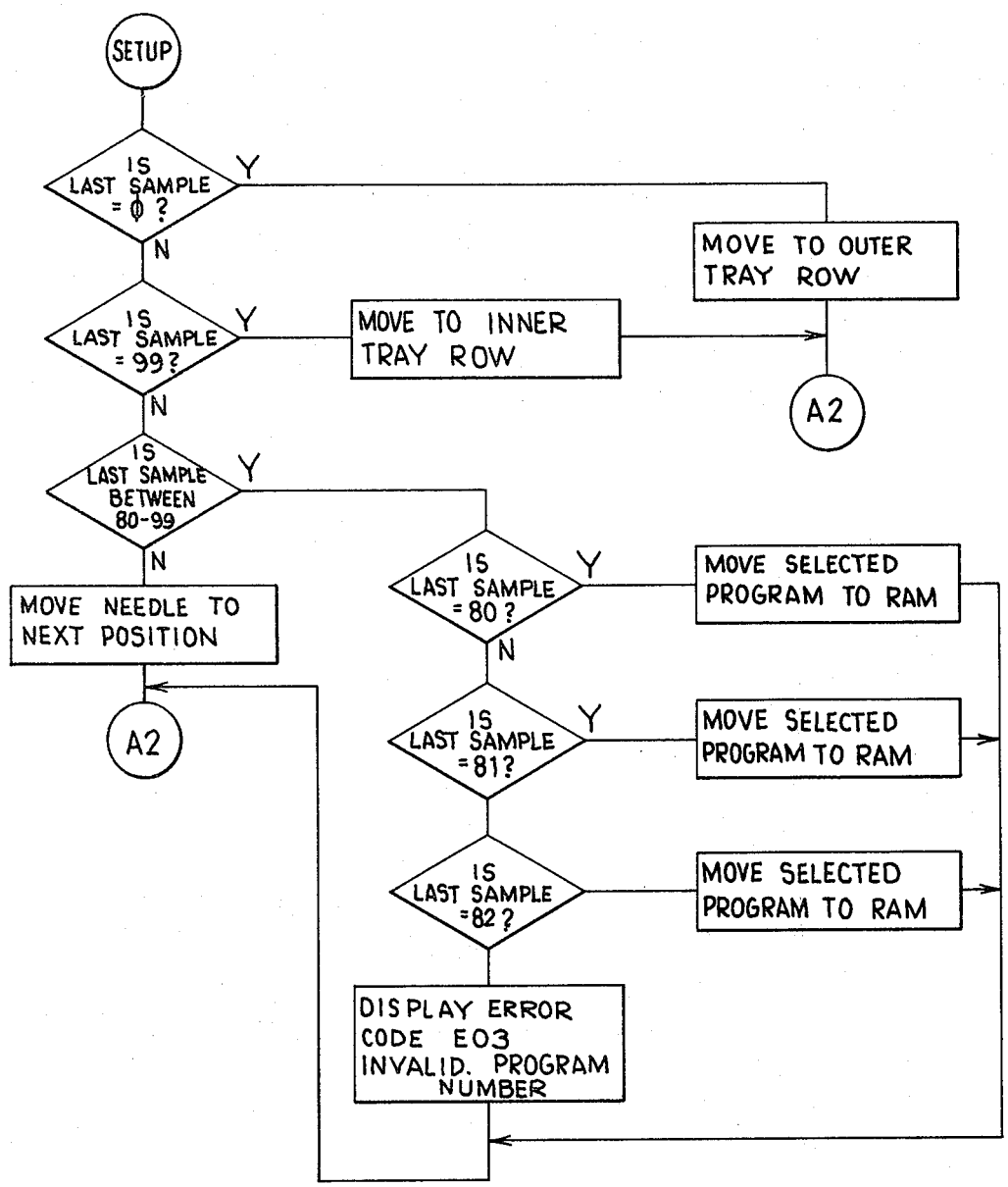

However, in the preferred embodiment shown, the above-described apparatus is controlled by a microprocessor circuit schematically indicated at 350 in FIG. 14.

Figure 10:
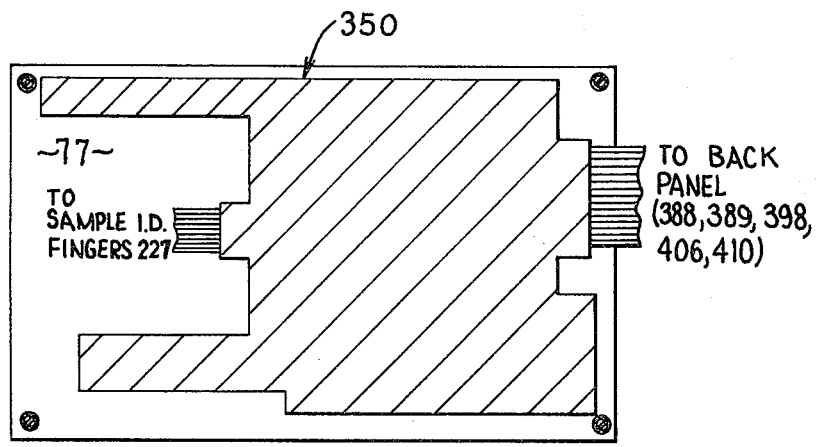
FIG. 10 and FIG. 11 are diagrammatic elevational views respectively showing interior front and rear circuitry panels.

The microprocessor circuit 350 may be conventional and here employs an Intel 8085 central processing unit, a 2K programmable read only memory (Intel 2716 EPROM), a 256 bytes random access memory (RAM) and timers which are conventionally interconnected and indicated by the block 351, and further employs an input-output port unit indicated by block 352 and which in one embodiment includes an Intel 8155 twenty-two line I/O port and an Intel 8255 twenty-four line I/O port with outputs suitably buffered and provided with latches as needed, all in accord with conventional internal microprocessor circuit practice. The microprocessor circuit 350 is, as schematically indicated in FIGS. 5 and 10, mounted on the interior front panel 77 and supplied dc operating potential from the conventional five volt power supply 233. As schematically indicated by the block 355 in FIG. 14, the microprocessor circuitry 50 is connected to receive, in parallel, the binary input signal from the tray position sensing (sample identification) fingers 227 (FIG. 7) engaging the binary coded disk 228, to indicate which sample container location on the tray 101 is in position for sampling by the probe 52. Block 355 also includes front panel switches 361, 362 and 363 (FIG. 8) mounted on the front panel 72 which are settable by the human operator to provide desired time spans for the sample, chromatography and rinse times through the microprocessor circuitry 50. A further thumb wheel switch 364 on the front panel is presettable by the operator to form the microprocessor circuit of the number (here from 0 to 80) of the last sample container on the tray 101 which is to be sampled by the probe 52 in an automatic sampling sequence involving sequential sampling of a desired number of sample containers beginning with one brought to the sampling position adjacent the probe 52 by rotation of the tray 101 by the human operator. Further ones of the front panel switches indicated at 355 in FIG. 14 include an auto/manual/set-up switch 365 and start switch 366.

The microprocessor circuit 350 provides a tray position (sample container position identification) display 371 on the front panel 72 (FIG. 8) which displays the appropriate decimal number between 1 and 80 (for example 15) corresponding to the container being sampled by the probe 52.

The microprocessor circuit 350 provides further outputs to certain front panel time displays 372 comprising alternatively illuminated light sources 374, 375 and 376 which, when illuminated, indicate that the microprocessor circuit 350 is timing either the sample interval, chromatography interval, or rinse interval, respectively. Such time displays further include a digital readout 377 with the time remaining in the particular sample, chromatography, or rinse interval being timed. Referring to the schematic representation at FIG. 5, it will be seen that signals are passed from the front panel inputs 355 to the microprocessor circuit 350 on the interior circuit board panel 77 and, correspondingly, output signals are applied from the microprocessor circuit 350 to the output devices 371, 372 on the front panel 72 through conventional multiple pin plug and socket connectors schematically indicated at 381 and 382 disposed between the front panels 72 and 77.

Figure 9:
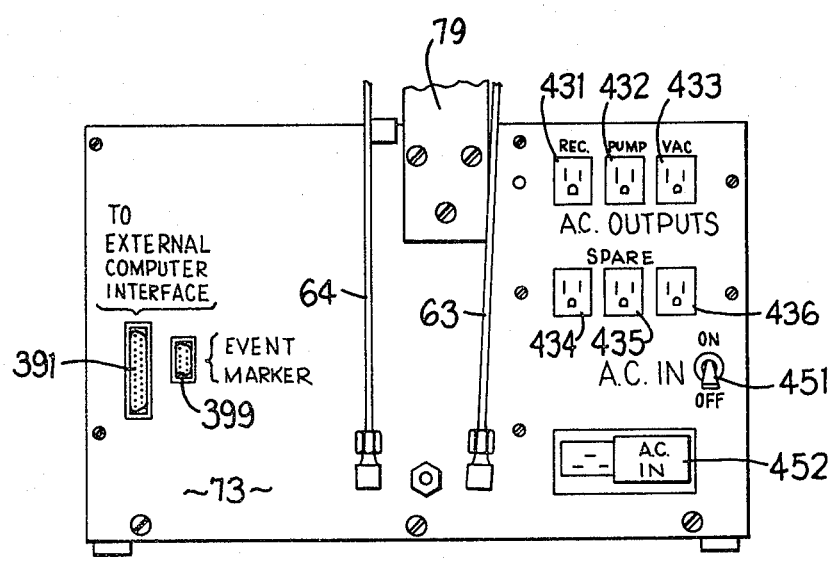
FIG. 9 is a rear view of the FIG. 2 sampler.

The microprocessor circuit 350 has a plurality of outputs to devices on the back printed circuit board panel 78 and back panel 73, carried by a flexible flat cable 386 (FIG. 5) terminated in conventional multi pin releasable connectors. These outputs include an eight bit parallel path 388, providing a second sample I.D. output from the microprocessor circuit 350, and a buffered inject signal conductor 389, which are applied through a conventional connector 391 (FIG. 9) on the back of the back panel 73 and thence through a multiconductor cable schematically indicated at 392 (FIG. 1) to the interface 393 of an external (host) computer 394 provided for conventionally assimilating analogue data appearing on a line or lines 396 from the chromatography detector 19 and conventionally generating outputs (such as typed reports, data storage on disks, or the like) recording the results of chromatography runs on successive samples.

Simultaneously with the generation of the inject signal on line 389, the microprocessor circuit 350 produces an event marker pulse which is applied through a conductor 398 (FIG. 14) and a releasable connector 399 on the back panel 73 (FIG. 9) to apply a corresponding pulse 401 to the trace 402 made by the stylus 38 of the recorder 16 (FIG. 1) and marking the switching by the valve 13 of a sample into the chromatography column 18, that is marking the beginning of a chromatography run for one sample. Subsequently, the chromatography detector 11, at a time depending on the composition of the sample, will produce the peak 403 in trace 402, wherein the spacing of the marker 401 and peak 403 provide an indication of the composition of the chromatography sample. The event marker and inject signal on lines 389 and 398 thus preferably are generated simultaneously with injection of a sample into the column 18, and serve as time markers respectively for the host computer 394 and analog recorder 16.

In the embodiment shown, the external computer interface 393 normally provides an enable signal on a line 406 (FIGS. 1 and 14) which indicates the host computer 394 is operating satisfactorily and which is applied through the back panel connector 391 (FIG. 9) to the microprocessor circuit 350. The absence of this enable signal informs the microprocessor that the host computer 394 is down and permits the microprocessor circuit 350 to terminate further operation of the chromatography apparatus until repair can be made.

Figure 11:
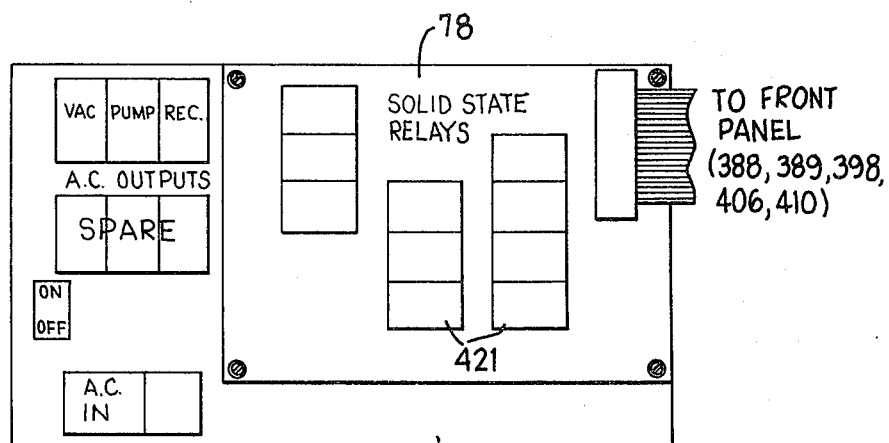

The microprocessor circuit 350 provides further outputs through a plurality of parallel control lines 410 to solid state relays 421 mounted on the back panel printed circuit board 78 (FIG. 11) and which in turn respectively control application of ac power to back panel ac output receptacles 431-436 into respective ones which are plugged the motors and/or circuitry of the mobile phase pump 17, recorder 16 and vacuum (sample) pump 46 for controlling operation thereof. Further ones of the rear panel solid state relays 421 control ac output to the above-described solenoid valves 301 and 306-308 of FIG. 6 (and solenoid valves 309 and 310 if provided to use the FIG. 12 modification).

In the FIG. 14 embodiment, the logical sequence of events in the apparatus is controlled by a program in the microprocessor circuit 350. In one embodiment the program employed a table-driven timer scheme to provide automatic sequencing through the FIG. 13 time chart.

In the FIG. 14 embodiment when the apparatus is first powered on, as by manual turning on of the ac on-off switch 451 controlling application of ac power from line input 452 (FIG. 9), the program is arranged to initialize the hardware and software to a known condition. The program first moves a copy of the timer table from the EPROM to the RAM in the block 351 (FIG. 14). This is done in view of the fact that the program modifies the table during operation and it thus must be in a writable area of the memory. Next, the input/output ports at 352 are initialized and programmed for their respective type functions. Following this, all ac solid state relays 421 are turned off. The program now cycles the sample arm 148 to an initial rinse position, with the probe 52 immersed in rinse receptacle 59 (pressure fluid cylinder 176 fully extended and vertical pressure fluid cylinder 126 retracted as in FIG. 3 and the outer container ring 102 of the tray 101 is selected) and pressure fluid cylinder 216 (FIG. 5) extended to its dotted line position). At this point the program enters a wait loop. The circumferential position of the sample tray 101 is monitored by the microprocessor circuitry 50 from the parallel signal pattern produced by the sample identification fingers 227 engaging the binary conducted pattern on the under side of the disk 228 (FIG. 7) and the resulting sample number is displayed by the microprocessor 350 on the front panel tray position display 371. It will be noted that the circumferential tray position can be manually shifted clockwise, despite the abovementioned full extension of the piston rod 181 and hence full leftward positioning of ratchet arm 241 (positions E in FIG. 5) since a modest clockwise force on the sprocket 116 will cause the teeth thereon to cam the ratchet arm end 243 and pivot the ratchet arm 241 to compress the spring 251 enough to allow a desired number of sprocket teeth to be rotated past the ratchet arm end 243. In FIG. 5 this cammed out of the way latter position of ratchet arm 241 is indicated at C, the indicated lateral positions I' and E' corresponding to its longitudinal positions I and E, respectively, at the beginning and end of its normal one-tooth clockwise incrementing of the sprocket 116 occurring in each normal FIG. 13 cycle hereafter discussed. The spring-loaded detent ball 236 also is resiliently displaced by successive teeth to permit a modest clockwise force to manually advance the tray 101 and sprocket wheel 116 to locate a desired initial container location on the ring 102 at the sampling position S (FIG. 2).

The foregoing initial program operation assumes, of course, that the apparatus has been readied for operation, by connecting the sampler 14 to an ac supply, turning on the ac on-off switch 451 on the back panel at 73, providing rinse liquid to the receptacle 59, placing sample containers as desired on the sample tray 101, and so forth.

In any event with the program in wait loop, the below described pressing of the front panel start switch 366 (FIG. 8) takes the program out of wait loop and into one of three different modes, auto, manual or set-up, depending on the corresponding of the front panel mode switch 365. Normally the set-up mode is selected first.

In set-up mode the ac power to the recorder 16 and mobile phase pump 17 are turned on. The time remaining display on front panel 72 displays 000 and the tray position display on the front panel 72 displays the number of the sample container at the sampling position S, which will be a number between 1 and 40 if the cylinder 216 is set to cause sampling at the outer sampling tray ring 102 or a number between 41 and 80 if the cylinder 216 is set to cause sampling of containers in the inner ring 103.

In the set-up mode, a momentary depression of the start switch causes the microprocessor circuit 350 to shift the sample probe 52 through one movement of its cycle of movements, for example moving the probe 52 up out of a container on the sample tray 101 (by extending the vertical pressure fluid cylinder 126) or moving the raised probe 52 back from sampling position to overlie the rinse receptacle 59 (by extending the cylinder 176) or dropping the probe 52 down into the rinse receptacle 59 (by retracting the vertical cylinder 126) or reversing of any one of the foregoing steps. In this way, the probe 52 can be stepped through its six-step cycle by corresponding manual sequential depressions of the front panel start switch. This permits the operator to make sure that the probe 52, sample containers, sample stripper arm, rinse receptacle, etc. are properly positioned. Also, with the probe 52 raised and forward (above the sample position S) the sample tray 101 can be rotated freely either clockwise or counterclockwise to the desired sample in that the ratchet arm is entirely disengaged from the sprocket 116.

In the set-up mode also, the program checks the front panel last sample switch 364. If it is set at 00, the program permits the cylinder 216 (FIG. 5) to remain in its dotted line extended position, selecting the outer sampling tray ring 102 occupied by container positions 1–40. On the other hand, if the last sample switch 364 is set at 99, the program causes the corresponding rear panel solid state relay 421, solenoid valve 308 and cylinder 216 to withdraw the forked wedge 219 (so that the cylinder 176 when retracted would place the probe 52 above the inner sampling tray ring 103 occupied by container positions 41–80). The number of samples for assay is then selected by setting the last sample stop thumb wheel switch on the front panel. Set-up is then completed.

The operator then shifts the mode switch to select either automatic or manual operation. After selecting, for example, automatic mode, the operator presses the front panel start switch and the microprocessor circuit is programmed to then carry out the timing cycle of FIG. 13 from time period T$\emptyset$ to time period T$\emptyset$ for each of the series of samples carried on the tray until the last sample set on the last sample switch 364 is reached. More particularly, upon actuation of the start switch in the automatic mode, the microprocessor circuitry 50 begins timing out the series of time intervals T$\emptyset$, T4, T5, . . . for a given sample and carries out the apparatus actuations shown in FIG. 13. Thus, prior to the initial time T$\emptyset$ in the FIG. 13 cycle the microprocessor circuitry 50 reads the thumb wheel time switches 361, 362 and 363 on the front panel and uses these values to update the timer table in the memory of microprocessor circuit 350 as to the desired sample, chromatography, and rinse times selected by the front panel switches. The first timer cycle T$\emptyset$ is started and the program waits for the microprocessor circuit 350 to time out at the end of time T$\emptyset$.

Following the end of time T$\emptyset$, the microprocessor circuit 350 times, in sequence, intervals T4, T5 and T6 during which, in sequence, it causes ones of the solid state relays 421 to act through the corresponding solenoid valves and pressure fluid cylinders of FIG. 6 to, in sequence, raise probe 52 (if in its down position) move the probe 52 forwardly to a position above the sampling position at the selected one of rings 102 and 103 (if the probe is not already in that position) and then move the probe 52 downward into the corresponding sample container on preselected ring 102 or 103. Thus, it is immaterial where the probe 52 is initially placed at the time of selection of the automatic mode and actuation of the start switch because the microprocessor circuit in time periods T4, T5 and T6 will assure delivery of the probe 52 to its downward sampling position in engagement with the first container to be sampled.

Figure 13:
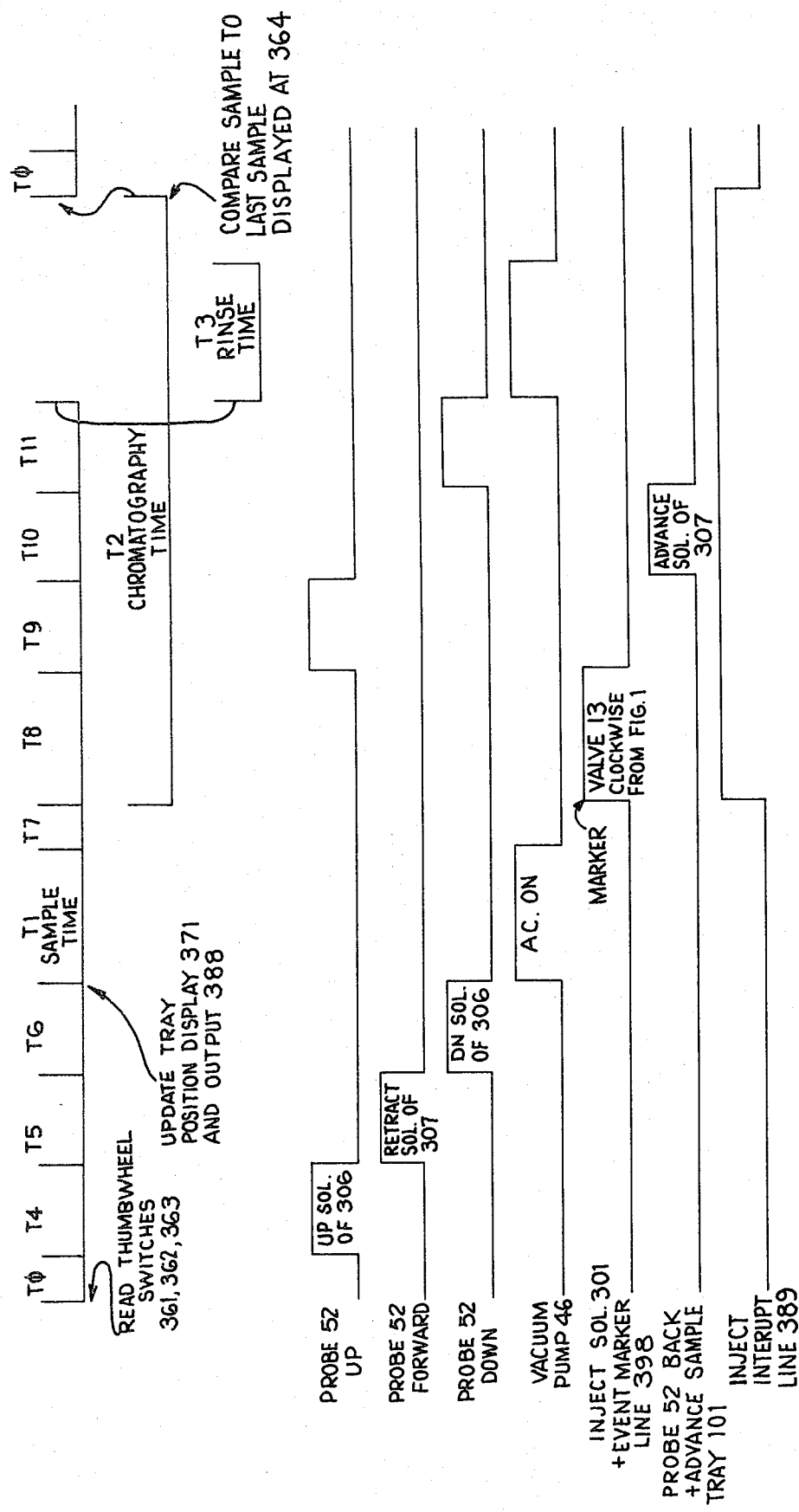
FIG. 13 is a timing diagram for chromatographic analysis of one sample by the FIG. 1 apparatus.

The times T$\emptyset$, T1, T2 . . . T11 timed by the microprocessor 350 do not occur in numerical order, but rather in the left to right order shown in FIG. 13. As seen in FIG. 13, the timed intervals vary in length and chromatography time T2 overlaps and extends beyond sequential intervals T8-T11 and T3, and indeed until the beginning of a next cycle, namely the beginning of a second starting interval T$\emptyset$.

Following the above-described intervals T$\emptyset$, T4, T5 and T6, the memory of the microprocessor is updated by the fingers 227 and in view of the position of the forked cylinder 216 earlier determined by the 00 or 99 setting of the last sample switch 364, such that position display 371 and the output path 388 are updated with the present sample engaged by the probe 52 at the beginning of sample time T1. During sample time T1 the microprocessor circuit applies ac power to the vacuum pump 46 to move liquid from the sampled container to lines 51, 44 and pump 46, to thereby load the loop 43 of the valve 13 therewith. Interval T7 provides a delay between turn-off of vacuum pump 46 and the simultaneous beginning of intervals T8 and chromatography time T2. During interval T8 the injection solenoid 301 and event marker line 398 are energized, the former placing the sample valve 13 90° clockwise from its FIG. 1 solid line position so that mobile phase liquid from pump 17 will shift the sample in loop 43 (now connected to ports 29 and 32) through line 33 into the column 18, accomplishing injection of the sample into the column and in fact initiates actual chromatography, which as above mentioned continues through the remaining intervals of the FIG. 13 cycle. At the end of interval T8 the valve 13 returns its sample loop 43 to its normal FIG. 1 solid line position such that mobile phase continues movement from pump 17 into the column 18 through the other valve loop 34 to continue to move the injected sample along the column 18. Subsequent intervals T9, T10 and T11 are those in which the microprocessor circuitry 50 causes the up solenoid of valve 306 to raise probe 52, causes the extend solenoid of valve 307 to advance the probe 52 back to its rinse liquid overlying position and advance the sample tray 101 one container interval, and causes the down solenoid of valve 306 to move the probe 52 down into the rinse liquid. During the next interval, the rinse time T3, the vacuum pump 46 is again actuated, this time to draw rinse liquid from the receptacle 59 through the vacuum pump 46 to cleanse the loop 43 of the sample valve 13. Eventually the chromatography interval T2 (coextensive with the appearance of the inject signal on line 389) times out, at which time the microprocessor circuit compares the sample at hand to the value appearing on the last sample display at 364 and if this "last sample" has not yet been run through the FIG. 13 cycle and hence injected into the column 18, the microprocessor circuit 355, due to the automatic position of switch 365, will repeat the FIG. 13 cycle. Thus, the FIG. 13 cycle repeats until the "last sample" displayed at 364 is processed.

Selection of the manual position of front panel switch 365 results in operation identical to that described above as to the automatic mode, except that in the manual mode only one injection (one FIG. 13 cycle) is carried out and after the chromatography time T2 has elapsed, the apparatus stops cycling.

It will be noted that selection of the set-up mode of front panel switch 365 at any time immediately resets the microprocessor circuit 350 to 0 time (the beginning of interval T∅) and will abort the previous FIG. 13 run. Initiation of a new FIG. 13 cycle then requires shifting of the mode switch 365 to either manual or automatic.

Additionally, the set-up mode can be used to select new program functions. The various timing programs (such as the events above discussed with respect to intervals T∅-T11) are in one embodiment stored in the EPROM and transferred to the RAM when the start button 366 is depressed. Certain settings of the last sample switch (as above discussed with respect to settings 00 and 99, can be used to select among various programs which can be initially stored in the EPROM.

Use of a programmable microprocessor circuit to control operation of the FIG. 1 apparatus would permit several alternative timing sequences (other than that described above with respect to FIG. 13) to be programmed into the microprocessor circuit and selected, for example by using of extra settings (numbers beyond 80, the number of sample positions on the tray 101 here shown) in the set-up mode. The number of the alternative programs thus selected could be shown in the time display window for verification purposes. Alternative programs could include the following:

1. Normal LC operation: selected by rotation of the last sample switch to position 80 and with mode switch in set-up mode start switch is depressed, providing the cycle above-discussed with respect to FIG. 13.

2. Sampling twice from the same sample vial, without rinse between duplicate samplings: The last sample switch is rotated to position 81 and, with the mode switch in set-up position, the start switch is depressed.

3. Special manual injection: The last sample switch is rotated to position 82 and activation of the start switch initiates the chromatography time T2 immediately, the sample and rinse cycles and related time intervals not being used. Various other alternative programs can be devised as desired and implemented with the disclosed apparatus.

It is also contemplated that the time display window 377 could additionally be used to display certain error codes, such as E01 (rinse or sample time set at 0 in auto mode), E02 (external enable line 406 not enabled), E03 (invalid program number selected at last sample switch 364), etc.

While the operation of the sampler 14 has been disclosed above, same is summarized as to one embodiment in the accompanying flow chart of FIGS. 15A–E.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privileged is claimed are defined as follows:

1. An apparatus for automatically establishing fluid communication between probe means and a plurality of containers presented in a controlled sequence to a sampling position, comprising:
   rack means adapted to hold said containers for movement into and out of said sampling position;
   hollow probe means supported by probe holding means and movably thereby into and out of said sampling position; and
   drive means connected to said rack means and to said probe holding means for effecting and controlling said movements thereof, said drive means including a first pressure fluid operated motor actuable for moving said probe means into and out of said sampling position for communication with containers thereat, and a second pressure fluid operated motor actuable for causing said rack means to move a desired one of said containers to said sampling position, said first and second pressure fluid operated motors being actuable independently of each other from a common source of pressure fluid, said first motor comprising a first pressure fluid cylinder actuable to move said probe means vertically, said first pressure fluid cylinder having a casing upstanding within said housing and a piston rod vertically reciprocable by pressure fluid, said second motor comprising a second pressure fluid cylinder with a casing horizontally extending from and supported on a vertical pivot axis fixed on said housing and a piston rod extending generally tangentially of said first pressure fluid cylinder and operatively connected to said first pressure fluid cylinder, and means for horizontally moving both said probe means and rack means for shifting said probe means between said sampling position and a rinse position, and for advancing said rack means to bring another container to said sampling position.

2. The apparatus of claim 1, including a housing, said rack means and probe means and sampling position being atop said housing, said first and second cylinders being within said housing, said housing containing solenoid valves through which said cylinders are connectible with said common pressure fluid source, a microprocessor circuit mounted within said housing adjacent said solenoid valves and connected through said solenoid valves for controlling all movements of said cylinders.

3. The apparatus of claim 1, including arm means pivoted on said upstanding first pressure fluid cylinder casing and having an outboard portion pivotally connected to said second pressure fluid cylinder for pivoting said arm means about the axis of said first pressure fluid cylinder in response to extension and retraction of said second pressure fluid cylinder and connected to support said probe means for pivoting of the latter therewith, ratchet arm means also pivotally connected with said outboard portion of said arm means for reciprocation thereby, means resiliently guiding said reciprocation of said ratchet arm means and a sprocket engaged by and responsive to reciprocation of said ratchet arm means for causing said rack means to advance containers to said sampling position.

4. The apparatus of claim 3, in which said rack means comprises a sample tray fixed coaxially to said sprocket by means supported for rotation about a vertical axis in said housing and protruding upward therethrough, and including detent means fixedly supported in said housing and cooperating with said sprocket for resiliently locating containers on said sample tray repeatably at said sampling position and holding same there prior to circumferential advancement of said sprocket by a reciprocation stroke of said ratchet arm means by said second pressure fluid cylinder.

5. The apparatus of claim 1, including a further pressure fluid cylinder horizontally fixed on said housing and actuable to interpose a wedge in the path of the piston rod of said second pressure fluid cylinder to reduce the horizontal range of swing of said probe means toward the rack means and thereby produce a second sampling position, said rack means comprising a rotationally movable sample tray having concentric first and second rings of container locations thereon, said first ring being surrounded by the second and passing through said first sampling position, said second sampling ring passing through said second sampling position.

6. The apparatus of claim 1, including a dash pot fixed within said housing opposite said second pressure fluid cylinder, arm means pivotable on said first pressure fluid cylinder casing and with an outboard portion pivotally connected to said second pressure fluid cylinder for pivoting thereby and located to abut said dash pot as said second pressure fluid cylinder nears the end of its extension, said arm means being connected to produce horizontal movement of said probe means between a rinse position and said sampling position and to advance said rack means.

7. The apparatus of claim 1, including arm means pivotable on said first pressure fluid cylinder casing and having an outboard portion swingable about said first pressure fluid cylinder casing, said outboard portion being pivotally connected to said second pressure fluid cylinder for pivoting said arm means thereby, said outboard portion being pivotally connected to ratchet arm means for stepwise moving of said rack means, said outboard portion including a first upstanding rod radially remote from said first pressure fluid cylinder casing and effecting said pivotal connection to said second pressure fluid cylinder and ratchet arm means adjacent the lower end thereof, a second upstanding rod radially spaced between said first upstanding rod and said first pressure fluid cylinder casing, a sample head fixed at one end to the upstanding piston rod of said first pressure cylinder for raising and lowering thereby and fixedly carrying said probe means at the remote end thereof, the upper end of said second upstanding rod being fixed to said sample head intermediate the ends of the latter for horizontally pivoting said sample head with said arm means, said second upstanding rod being slidable up and down with respect to said arm means for maintaining alignment of said sample head with said arm means during vertical reciprocation of said first pressure fluid cylinder, said first upstanding rod being vertically fixed with respect to said arm means and pivotally connecting said arm means with said ratchet arm means and second pressure fluid cylinder, said first upstanding rod carrying at its upper end, for pivotal adjustment about the axis of said first upstanding rod, sample stripper means including a sample stripper arm disposed along the vertical path of movement of said probe means for vertically guiding and stripping of containers from said probe means during vertical movement of said probe means with respect thereto and for horizontal pivoting with said probe means, said first upstanding rod being vertically fixed with respect to said arm means.

8. An apparatus for automatically establishing fluid communication between probe means and a plurality of containers presented in a controlled sequence to a sampling position, comprising:

rack means adapted to hold said containers for movement into and out of said sampling position;

hollow probe means supported by probe holding means and movable thereby into and out of said sampling position; and drive means connected to said rack means and to said probe holding means for effecting and controlling said movements thereof, said drive means including a first pressure fluid operated motor actuable for moving said probe means into and out of said sampling position for communication with containers thereat, and a second pressure fluid operated motor actuable for causing said rack means to move a desired one of said containers to said sampling position, said first and second pressure fluid operated motors being actuable independently of each other from a common source of pressure fluid, said first pressure fluid actuated motor comprising independently actuable horizontal and vertical pressure fluid cylinders for horizontally pivoting and vertically shifting said probe means, said second pressure fluid actuated motor comprising at least one further pressure fluid cylinder and ratchet arm means reciprocated thereby, said rack means comprising a rotatable sample tray and a sprocket in fixed rotationally driving relation with said sample tray and engageable by said ratchet arm means for circumferentially incrementing said sample tray by reciprocation of said further pressure fluid cylinder.

9. An apparatus for automatically establishing fluid communication between probe means and a plurality of containers presented in a controlled sequence to a sampling position, comprising:

rack means adapted to hold said containers for movement into and out of said sampling position;

hollow probe means supported by probe holding means and movable thereby into and out of said sampling position, and drive means connected to said rack means and to said probe holding means for effecting and controlling said movements thereof;

a housing containing said drive means and surmounted by said rack means and probe means;

a center mounting block fixed within said housing and flanked in spaced relation by a horizontally fixed, vertically extensible pressure fluid cylinder and a horizontally fixed vertical axis support on which said rack means is rotatably supported;

a contact finger bracket fixed atop said center mounting block and coactive with a binary disk rotatable in fixed relation with said rack means for identifying containers presented to said sampling position;

a sprocket rotatable with said rack and ratchet arm means extending between said vertically extensible pressure fluid cylinder and adjacent one end thereof and having an opposite end engageable with teeth of said sprocket for circumferentially incrementing said rack means, said center mounting block including means resiliently guiding the central portion of said ratchet arm means for reciprocation therethrough;

detent means on said center mounting block for engaging said sprocket to precisely align a container thereon with the sampling position and to prevent unintended rotation of said rack means in the absence of actuation by said ratchet arm means.

10. The apparatus of claim 9, in which said rack means comprises a sample tray having radially inner and outer rings of container locations thereon, a horizontal pressure fluid cylinder having an extensible portion and extending adjacent said center mounting block and engageable with a pivot arm for reciprocably driving said ratchet arm means, means supporting said probe means for pivoting with said pivot arm in response to reciprocation of said horizontal pressure fluid cylinder, and including a further horizontal pressure fluid cylinder supported on said center mounting block and extensible to insert a wedge into the path of the extensible portion of said first mentioned horizontal pressure fluid cylinder to change one end of the stroke range thereof and thereby cause the probe means to swing to a sampling position on the outer rather than the inner ring of containers of said rack means.

11. The apparatus of claim 10, including means fixing said vertically extensible pressure cylinder and center mounting block on a floor surface low in said housing, and including first, second, and third electrically actuable pressure fluid flow control valves upstanding from said floor surface adjacent to, and controlling pressure fluid flow to, said vertically extensible pressure fluid cylinder, said first mentioned horizontal pressure fluid cylinder and said further horizontal pressure fluid cylinder, a fourth electrically actuated pressure fluid control valve upstanding from said floor surface, and an automatic injection valve mounted on said housing and supplied pressure fluid under control of said fourth valve for controlling positioning of said automatic injection valve, said automatic injection valve controlling liquid flow from said probe means to selected locations for sample analysis or rinse liquid disposal.

12. An apparatus for automatic sampling of containers presented in a controlled sequence to a sampling position, comprising:

a housing;

rack means adapted to hold said containers for movement into and out of said sampling position;

hollow probe means supported by probe holding means and movable thereby into and out of said sampling position;

motor means within said housing and connected to said rack means and to said probe holding means for effecting and controlling said movements thereof;

a microprocessor circuit mounted within said housing adjacent said motor means and connected thereto for controlling movements of said motor means in a preselectable sequence, said housing including exterior front and rear panels, said exterior front panel carrying manually settable control data inputs and information display means, interior front and rear panels disposed within said housing respectively adjacent said exterior front and rear panels, said motor means being pneumatic and being disposed between said interior panels, said interior front panel mounting said microprocessor circuit, connecting means between said front panels for interconnecting said microprocessor circuit with said control data inputs and information display means on said exterior front panel, a circuit voltage supply mounted in said housing adjacent said interior front panel for supplying operating potential to said microprocessor circuit thereon, an external voltage supply input connection on said exterior rear panel, controllable relay means mounted on said interior rear panel and controllable for applying said external voltage to operate said motor means, conductor means connecting control inputs of said controllable relay means to outputs of said microprocessor circuitry on said interior front panel.

13. The apparatus of claim 12, in which said motor means includes solenoid valves and pneumatic motors driven thereby and in turn defining the sole motor power sources for said rack means and probe means, said circuit voltage supply being a low dc voltage supply, said external voltage being an ac voltage, said controllable means being solid state ac controlling relays controllable for applying ac operating potential to said solenoid valves and having dc control inputs controlled by said microprocessor circuitry.

14. Apparatus for automatic sampling of containers presented in a controlled sequence to a sampling position, comprising:

a housing;

a rack adapted to hold said containers and mounted for moving of said containers into and out of the sampling position;

a hollow probe supported by probe holding means and movable into and out of the sampling position;

motor means within the housing and connected to the rack means and to the probe holding means for effecting and controlling the movements thereof;

a microprocessor circuit mounted within said housing adjacent the motor means and connected thereto for controlling movements of said motor means in a preselectable sequence, said microprocessor circuit including a programmed microprocessor;

front panel switches mounted on the front panel of said housing and manually actuable for applying to the microprocessor the number of the last position on said rack to be sampled, and the duration of sample time, chromatography time and rinse time intervals to be timed by said microprocessor circuit;

rack position means disposed adjacent said rack for sensing the instantaneous position thereof and applying to said microprocessor a digital signal pattern indicating instantaneous portion of the rack, said front panel carrying a digital display driven by said microprocessor and indicating the instantaneous position of said tray;

a digital display on said front panel indicating the time remaining in the then running one of said sample time, chromatography time and rinse time intervals, said time remaining display being driven by an output of said microprocessor, the microprocessor having a plurality of control outputs;

a chromatography column and detector connected with a recorder to indicate the results of a chromatography measurement by the column;

means providing an output event marker from said microprocessor to said recorder to differentiate between recordings for different samples fed to said column;

a sampling valve loadable with a quantity of sample from a given container on said rack and actuable for applying said quantity of sample of said column and pump means for transferring said quantity of sample from said container on said rack through said sampling valve to said column;

means controlling operation of said pump means, recorder and sampling valve in response to said last-mentioned outputs of said microprocessor to cycle same through said sample time, chromatography time and rinse time for each container sampled by said hollow probe means, said last-mentioned outputs of said microprocessor also being connected to control sequencing of said rack means and hollow probe means in coordination with said pump means, recording and sampling valve.

15. The apparatus of claim 14, including an external computer interface, lines for transferring from said microprocessor to said external computer interface sample identification data and signals indicating the time at which a sample is injected into the column, a line from said external computer interface to said microprocessor for providing an enable signal when an external computer is ready to receive data from the microprocessor, means providing the output from said detector to said external computer interface for directly providing detector output analog data thereto for processing by the external computer in relation to the sample identification data provided by said microprocessor, such that an external computer can be used for generation of reports, for storing test data, and similar uses, but wherein said microprocessor in said housing controls both sampling of said containers on said rack and operation of said chromatography column and detector.

* * * * *

UNITED STATES PATENT AND TRADEMARK OFFICE
CERTIFICATE OF CORRECTION

PATENT NO. : 4 429 584

DATED : February 7, 1984

INVENTOR(S) : William F. Beyer, Harry S. Dankert and James C. English

It is certified that error appears in the above-identified patent and that said Letters Patent is hereby corrected as shown below:

```
Column  1, line 18;   change "samples" to ---samplers---.
           line 55;   delete "and purposes" (second occurrence).
Column  3, line  1;   change "volumn" to ---volume---.
Column  5, line 63;   change "receptable" to ---receptacle---.
Column 12, line 34;   change "men ory" to ---memory---.
           line 42;   after "selected" delete ")".
Column 16, line 22;   change "privileged" to ---privilege---.
Column 21, line  4;   change "portion" to ---position---.
```

Signed and Sealed this

Twenty-third Day of October 1984

[SEAL]

Attest:

GERALD J. MOSSINGHOFF

Attesting Officer   Commissioner of Patents and Trademarks